US012203130B2

(12) United States Patent
Krylov

(10) Patent No.: US 12,203,130 B2
(45) Date of Patent: Jan. 21, 2025

(54) BINDER SELECTION USING CAPILLARY ELECTROPHORESIS

(71) Applicant: Sergey N. Krylov, Toronto (CA)

(72) Inventor: Sergey N. Krylov, Toronto (CA)

(*) Notice: Subject to any disclaimer, the term of this patent is extended or adjusted under 35 U.S.C. 154(b) by 784 days.

(21) Appl. No.: 17/416,063

(22) PCT Filed: Dec. 16, 2019

(86) PCT No.: PCT/CA2019/051820
§ 371 (c)(1),
(2) Date: Jun. 18, 2021

(87) PCT Pub. No.: WO2020/124213
PCT Pub. Date: Jun. 25, 2020

(65) Prior Publication Data
US 2022/0042079 A1    Feb. 10, 2022

Related U.S. Application Data

(60) Provisional application No. 62/782,720, filed on Dec. 20, 2018.

(51) Int. Cl.
*C12Q 1/6816* (2018.01)
*C40B 30/04* (2006.01)
*G01N 27/447* (2006.01)

(52) U.S. Cl.
CPC ........... *C12Q 1/6816* (2013.01); *C40B 30/04* (2013.01); *G01N 27/44747* (2013.01); *G01N 27/44791* (2013.01)

(58) Field of Classification Search
CPC ........... C12Q 1/6816; C40B 30/04; G01N 27/44747; G01N 27/44752; G01N 27/447891; G01N 27/44791; C07K 1/26
See application file for complete search history.

(56) References Cited

U.S. PATENT DOCUMENTS 5,096,554 A * 3/1992 Chin ................ G01N 27/44747
204/451
5,116,471 A * 5/1992 Chien .............. G01N 27/44773
204/453

(Continued)

FOREIGN PATENT DOCUMENTS

CA    2375606 A1    2/2001
CA    2394847 A1    6/2001

(Continued)

OTHER PUBLICATIONS

Chapter 23, Explanatory Chapter: Qunatitative PCR by Jessica Dymond in Methods in Enzymology, vol. 529, 2013 Elsevier (Year: 2013).*

(Continued)

*Primary Examiner* — Alexander S Noguerola
(74) *Attorney, Agent, or Firm* — Thomas | Horstemeyer, LLP

(57) ABSTRACT

A method of capillary electrophoresis is provided for binder selection. In an embodiment, a capillary electrophoresis method comprises selecting an electroosmotic flow (EOF) in a capillary such that at least one target-binder (TB) complex has a target-binder velocity vector (vTB) co-directed with an electric field vector (E) and at least one non-binder (N) has a non-binder velocity vector (vN) in the opposite direction to the electric field vector (E); introducing a sample comprising the at least one target-binder (TB) complex, the at least one non-binder (N), and at least one running buffer into a capillary inlet of the capillary; applying an electric field directed from the capillary inlet to a capillary outlet of the capillary to separate the at least one target-binder (TB) complex from the at least one non-binder (N); and detecting the at least one target-binder complex.

34 Claims, 17 Drawing Sheets

(56) References Cited

U.S. PATENT DOCUMENTS

| | | | |
|---|---|---|---|
| 5,262,031 | A | 11/1993 | Lux et al. |
| 5,264,101 | A * | 11/1993 | Demorest ........ G01N 27/44752 |
| | | | 204/601 |
| 5,296,116 | A | 3/1994 | Guttman |
| 5,358,618 | A | 10/1994 | Eweing et al. |
| 5,573,905 | A | 11/1996 | Lerner et al. |
| 5,611,903 | A | 3/1997 | Janssens et al. |
| 5,630,924 | A | 5/1997 | Fuchs et al. |
| 5,639,603 | A | 6/1997 | Dower et al. |
| 5,708,153 | A | 1/1998 | Dower et al. |
| 5,723,598 | A | 3/1998 | Lerner et al. |
| 5,789,162 | A | 8/1998 | Dower et al. |
| 5,958,202 | A | 9/1999 | Regnier et al. |
| 6,060,596 | A | 5/2000 | Lerner et al. |
| 6,140,493 | A | 10/2000 | Dower et al. |
| 6,305,486 | B1 * | 10/2001 | Polzin .................... B60K 17/10 |
| | | | 180/242 |
| 7,070,928 | B2 | 7/2006 | Liu et al. |
| 7,223,325 | B2 | 5/2007 | Landers et al. |
| 7,223,545 | B2 | 5/2007 | Liu et al. |
| 7,277,713 | B2 | 10/2007 | Landschaft et al. |
| 7,413,854 | B2 | 8/2008 | Pedersen et al. |
| 7,442,160 | B2 | 10/2008 | Liu et al. |
| 7,479,472 | B1 | 1/2009 | Harbury et al. |
| 7,491,160 | B2 | 2/2009 | Vestola et al. |
| 7,557,068 | B2 | 7/2009 | Liu et al. |
| 7,704,925 | B2 | 4/2010 | Gouliaev et al. |
| 7,771,935 | B2 | 8/2010 | Liu et al. |
| 7,807,408 | B2 | 10/2010 | Liu et al. |
| 7,998,904 | B2 | 8/2011 | Liu et al. |
| 8,017,323 | B2 | 9/2011 | Liu et al. |
| 8,119,798 | B2 | 2/2012 | Clark |
| 8,183,178 | B2 | 5/2012 | Liu et al. |
| 8,224,582 | B2 | 7/2012 | Krylov et al. |
| 9,261,482 | B1 | 2/2016 | Henry et al. |
| 2008/0314751 | A1 | 12/2008 | Bukshpan et al. |
| 2012/0053901 | A1 | 3/2012 | Arefeen et al. |
| 2014/0315762 | A1 | 10/2014 | Keefe et al. |
| 2017/0130218 | A1 | 5/2017 | Lin |
| 2018/0246056 | A1 | 8/2018 | Boeke et al. |

FOREIGN PATENT DOCUMENTS

| | | |
|---|---|---|
| CA | 2394847 C | 6/2001 |
| CN | 108613862 A | 10/2018 |
| WO | 95/11451 A1 | 4/1995 |
| WO | 96/33412 A1 | 10/1996 |
| WO | 00/79260 A1 | 12/2000 |
| WO | 2003/102212 A3 | 12/2003 |
| WO | 2017/126646 A1 | 7/2017 |
| WO | 2018/008945 A1 | 1/2018 |

OTHER PUBLICATIONS

Corradini et al., "Dependence of the Electroosmotic Flow in Bare Fused-Silica Capillaries from pH, Ionic Strength and Composition of Electrolyte Solutions Tailored for Protein Capillary Zone Electrophoresis," Chromatographia 2003, 58, November (No. 9/10), pp. 587-596 (Year: 2003).*

Bao, Jiayin, et al., "Predicting Electrophoretic of Protein-Ligand Complexes for Ligands from DNA-Encoded Libraries of Small Molecules," Anal. Chem. (2016) vol. 88, pp. 5498-5506.

Berezovski, Maxim, et al., "Nonequilibrium Capillary Electrophoresis of Equilibrium Mixtures: A Universal Tool for Development of Aptamers," J. Am. Chem. Soc., vol. 127, No. 9 (2005) pp. 3165-3171.

Berezovski, Maxim, et al., "Non-SELEX Selection of Aptamers," J. Am. Chem. Soc. vol. 128 (2006) pp. 1410-1411.

Ding, Weiliang, et al., "Capillary electrophoresis of anions at high salt concentrations," Electrophoresis vol. 19 (1998) pp. 2133-2139.

Drabovich, Andrei P., et al., "Selection of Smart Aptamers by Methods of Kinetic Capillary Electrophoresis," Anal. Chem. vol. 78 (2006) pp. 3171-3178.

Drabovich, Andrei P., et al., "Selection of Smart Small-Molecule Ligands: The Proof of Principle," Anal. Chem. vol. 81 (2009) pp. 490-494.

Ellington, Andrew D. et al., "In vitro selection of RNA molecules that bind specific ligands," Nature vol. 346 (1990) pp. 818-822.

Evenhuis, Christopher J. et al., "Universal Method for Determining Electrolyte Temperatures in Capillary Electrophoresis," Anal. Chem. vol. 83 (2011) pp. 1808-1814.

Hayes, Mark A., et al., "Effects of Buffer pH on Electroosmotic Flow Control by an Applied Radial Voltage for Capillary Zone Electrophoresis," Anal. Chem. vol. 65 (1993) pp. 27-31.

Irvine, Doug, et al., "Systematic Evolution of Ligands by Exponential Enrichment with Integrated Optimization by Non-linear Analysis," J. Mol. Biol. vol. 222 (1991) pp. 739-761.

International Search Report and Written Opinion, PCT Application No. PCT/CA2019/051820, mailed Feb. 27, 2020 (9 pages).

Kanoatov, Mirzo, et al., "Analysis of DNA in Phosphate Buffered Saline Using Kinetic Capillary Electrophoresis," Anal. Chem. vol. 88 (2016) pp. 7421-7428.

Kochmann, Sven, et al., "Predicting efficiency of NECEEM-based partitioning of protein binders from nonbinders in DNA-encoded libraries," Electrophoresis, vol. 39 (2018) pp. 2991-2996.

Lipponen, Katriina, et al., "Stable neutral double hydrophilic block copolymer capillary coating for capillary electrophoretic separations," Electrophoresis, vol. 35 (2014) pp. 1106-1113.

Meagher, Robert J., et al., "End-labeled free-solution electrophoresis of DNA," Electrophoresis, vol. 26 (2005) pp. 331-350.

Melanson, Jeremy E., et al., "Dynamic capillary coatings for electroosmotic flow control in capillary electrophoresis," Trends in Analytical Chemistry, vol. 20, Nos. 6+7 (2001) pp. 365-374.

Mendonsa, Shaun D., et al., "In Vitro Evolution of Funcational DNA Using Capillary Electrophoresis," J. Am. Chem. Soc., vol. 26 (2004) pp. 20-21.

Mendonsa, Shaun D., et al., "In Vitro Selection of High-Affinity DNA Ligands for Human IgE Using Capillary Electrophoresis," Anal. Chem., vol. 76 (2004) pp. 5387-53920.

Musheev, Michael U., et al., "Stable DNA Aggregation by Removal of Counterions," Anal. Chem., vol. 85 (2013) pp. 10004-10007.

Musheev, Michael U., et al., "Non-uniform Velocity of Homogeneous DNA in a Uniform Electric Field: Consequence of Electric-Filed-Induced Slow Dissociation of Highly Stable DNA-Counterion Complexes," J. Am. Chem. Soc. vol. 135 (2013) pp. 8041-8046.

Tang, P.S., et al., "Selection of DNA Aptamers by Capillary Electrophoresis for Binding of Biomolecules and Bioimaging," Department of Chemistry, Faculty of Science, National University of Singapore (4 pages).

Wang, Jinpeng, et al., "Influence of Target Concentration and Background Binding on In Vitro Selection of Affinity Reagents," Plos One, vol. 7, Issue 8, (2012) (8 pages).

Waser, Jürg, "Quantitative Chemistry, a laboratory text," W. A. Benjamin, Inc., New York Amsterdam (1964) (3 pages).

Whatley, Harry, "Basic Principles and Modes of Capillary Electrophoresis," Clinical and Forensic Applications by Capillary Electrophoresis, (abstract) pp. 21-58.

Li, Sam, "Capillary Electrophoresis: Principles, practice, and Applications," Journal of Chromatography Library; Elsevier Science Publishers: The Netherlands vol. 52 (1991).

Patel, Kevin H., et al., "Simplied universal method for determining electrolyte temperatures in a capillary electrophoresis instrument with forced-air cooling," Electrophoresis vol. 33 (2012) pp. 1079-1085.

Podolin, Patricia L., et al., "In vitro and in vivo characterization of a novel soluble epoxide hydrolase inhibitor," Prostaglandins & other Lipid Mediators, 104-105 (2013) pp. 25-31.

Polson, Nolan A., et al., "Electroosmotic Flow Control of Fluids on a Capillary Electrophoresis Microdevice Using an Applied External Voltage," Anal. Chem. vol. 72 (2000) pp. 1088-1092.

Schneider, Bohdan, et al., "Hydration of the Phosphate Group in Double-Helical DNA," Biophysical Journal vol. 75 (1998) pp. 2422-2434.

Young, M.E., et al., "Estimation of Diffusion Coefficients of Proteins," Biotechnol. Bioeng. vol. 22 (2004) pp. 947-955.

(56) References Cited

OTHER PUBLICATIONS

Yufa, Roman, et al., "Emulsion PCR Significantly Improves Nonequilibrium Capillary Electrophoresis of Equilibrium Mixtures-Based Aptamer Selection: Allowing for Efficient and Rapid Selection of Aptamer to Unmodified ABH2 Protein," Anal. Chem vol. 87 (2015) pp. 1411-1419.
Office Action, issued by Canadian Intellectual Property Office, for Canadian Application No. 3,120,895 on Jul. 4, 2023 (4 pages).
Office Action, issued by Canadian Intellectual Property Office, for Canadian Application No. 3,120,895 on Jan. 16, 2023 (6 pages).
European Search Report, EP Application No. 19900023.3, mailed Jul. 26, 2022 (5 pages).
Krylova, Svetlana M., et al., "Mechanistic Studies on the Application of DNA Aptamers as Inhibitors of 2-Oxoglutarate-Dependent Oxygenases," Journal of Medicinal Chemistry, vol. 55, No. 7 (2012), pp. 3546-3552.
Kanoatov, M., et al., "Selection of aptamers for a non-DNA binding protein in the context of cell lysate," Analytica Chimica Acta, vol. 681, No. 1-2 (2010), pp. 92-97.
M. A. Clark et al., "Design, Synthesis and Selection of DNA-Encoded Small-Molecule Libraries", Nature Chemical Biology, (2009) vol. 5, pp. 647-772.
International Search Report for Application No. PCT/CA2019/051820 mailed Feb. 27, 2020.

\* cited by examiner $t_{R1}, t_{R2}$ : Retention time for each peak ($t_{R1} < t_{R2}$)
$W_{0.5h1}, W_{0.5h2}$ : Full width at half maximum (FWHM) of each peak
$W_1, W_2$ : Width of each peak Fig. 1 Two Adjacent Peaks Fig. 8A
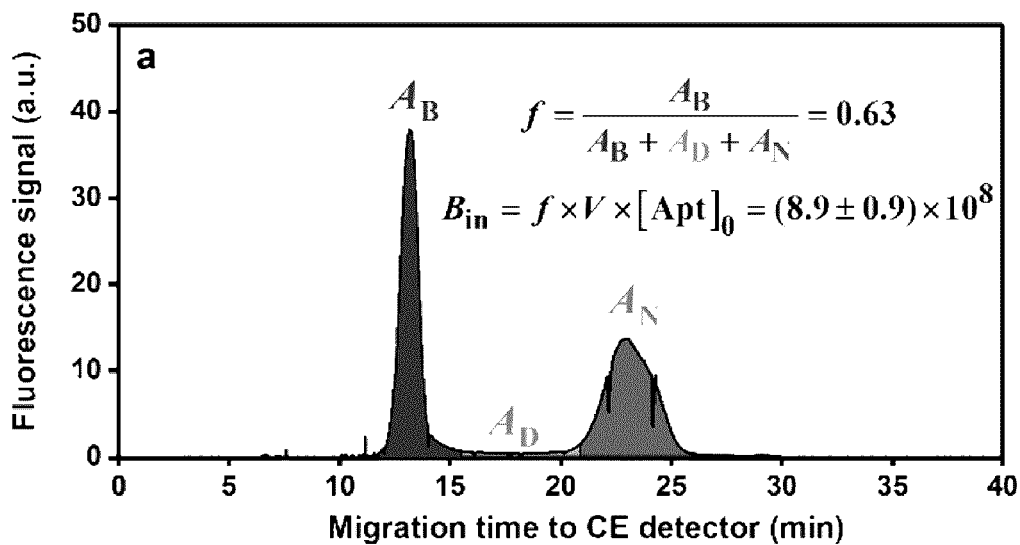
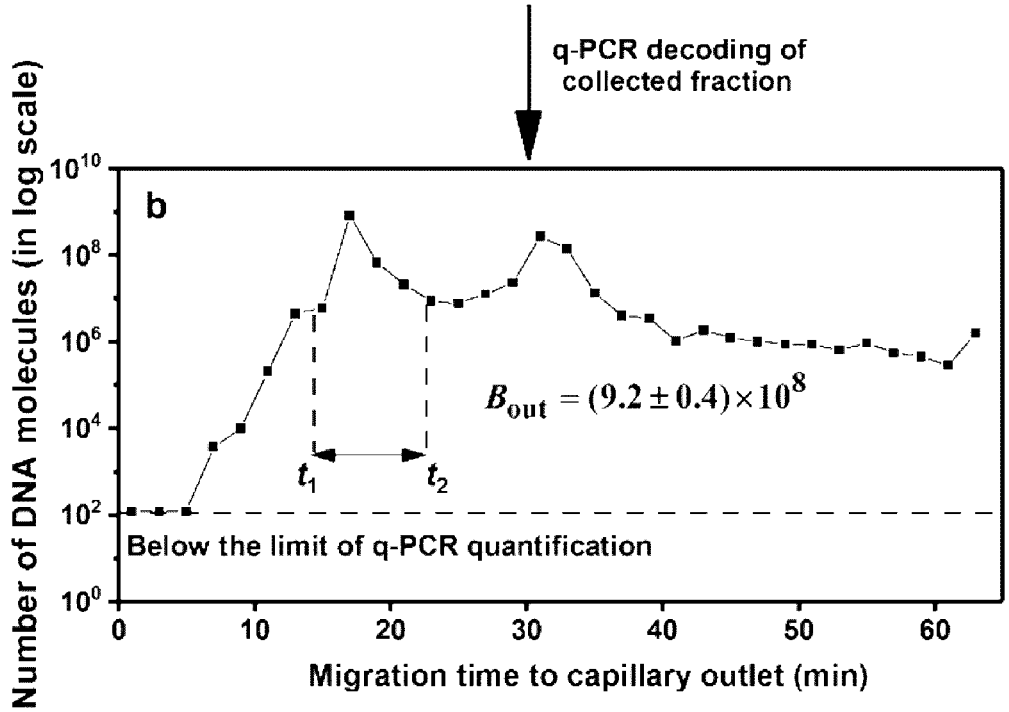
Fig. 8B

BINDER SELECTION USING CAPILLARY ELECTROPHORESIS

FIELD

The present disclosure relates to a method and system for binder selection, in particular, binder selection from oligonucleotide libraries using capillary electrophoresis (CE).

BACKGROUND

Oligonucleotide tagged combinatorial libraries were first described in the early nineties as sources of lead compounds for drug discovery (U.S. Pat. Nos. 6,140,493; 6,060,596; 5,789,162; 5,723,598; 5,708,153; 5,639,603; and 5,573,905) and methods were subsequently developed for making oligonucleotide tagged combinatorial libraries (e.g., U.S. Pat. Nos. 7,479,472; 7,070,928; 7,223,545; 7,442,160; 7,491,160; 7,557,068; 7,771,935; 7,807,408; 7,998,904; 8,017,323; 8,183,178; 7,277,713; 7,413,854; 7,704,925; 8,410,028; 8,598,089; U.S. Patent Application No. 2012/0053901; and U.S. Patent Application No. 2014/0315762).

A variety of lead compounds have been identified against targets of intense biological interest (e.g. Podolin et al., *Prostaglandins & Other Lipid Mediators* 2013, 25, 104-105; and U.S. Pat. No. 8,119,798), therefore, there is interest in oligonucleotide libraries, in general, including oligonucleotide tagged combinatorial libraries, such as oligonucleotide tagged molecules (e.g. oligonucleotide tagged drugs), and/or oligonucleotides alone, such as aptamers. Aptamers are single-stranded DNA or RNA (ssDNA or ssRNA) molecules. Compounds from the oligonucleotide libraries of molecules can bind target molecules tightly and selectively. Common binding targets include, for example, proteins, peptides, carbohydrates, and small molecules. Target recognition and binding can involve three-dimensional, shape-dependent interactions as well as hydrophobic and electrostatic interactions, base-stacking, and intercalation.

Oligonucleotides alone are typically selected from random-sequence oligonucleotide libraries in a process called systematic evolution of ligands by exponential enrichment (SELEX) (see FIG. 1A). SELEX involves iterated rounds of separation (partitioning) and polymerase chain reaction (PCR) amplification. In essence, the library is mixed and incubated with a target to allow oligonucleotide tagged molecules and/or oligonucleotides to bind to target molecules forming target-binder complexes. The target-binder complexes are partitioned from the unbound library (non-binders) by any of the available separation methods. The binders are dissociated from the target and amplified by PCR to constitute a binder-enriched library that is used in the next round of SELEX until the binder-to-non-binder ratio reaches a desired value, preferably much greater than unity. The publication, *Emulsion PCR Significantly Improves Nonequilibrium Capillary Electrophoresis of Equilibrium Mixtures-Based Aptamer Selection; Allowing for Efficient and Rapid Selection of Aptamer to Unmodified ABH2 Protein*, by Yufa et al., *Anal. Chem.* 2015, 87, 1411-1419 (see FIG. 1B), suggests that SELEX is inherently prone to failure because PCR preferentially amplifies non-binders, which are less structured oligonucleotide tagged molecules and/or oligonucleotides than binders and are, hence, more easily accessible to enzymes involved in the amplification, such as polymerases. As a result, SELEX enriches non-binders instead of binders if the efficiency of enriching binders in separation is lower than the efficiency of enriching non-binders in PCR amplification.

In FIGS. 1A and 1B, for example, it is assumed that binder selection is complete when binder-to-non-binder ratio (B/N) reaches 100 after m rounds of SELEX: $(B/N)_m \geq 100$. Then, according to the algebraic model of SELEX, the number of rounds, m, is:

$$m \geq \lceil \log\{(B/N)_0/100\}/\log\{(k_N/k_B)(Z_N/Z_B)^n\} \rceil \quad \text{eq. 1}$$

where $\lceil x \rceil$ represents a mathematical function that rounds x up to the nearest integer, $(B/N)_0$ is the binder-to-non-binder ratio in the starting DNA library, $k_B$ and $k_N$ are transmittances of separation for binders and non-binders, respectively, $Z_B$ and $Z_N$ are bases of the exponent describing PCR amplification of binders and non-binders, respectively, and n is the number of PCR cycles in one round of SELEX. The transmittance of non-binders, $k_N$, is a fraction of non-binders that transmits during separation. This fraction contaminates binders and creates non-binder background in the selection process.

According to eq. 1, SELEX fails (m approaches $+\infty$ or becomes negative) when:

$$(k_N/k_B)(Z_B/Z_N)^n \leq 1 \quad \text{eq. 2}$$

Ideally, $k_B=1$, $k_N=0$, and $Z_B=Z_N=2$; however, in reality, $k_B<1$, $k_N>0$, and $Z_B<Z_N$. As an example, for typical values of $k_B/k_N=10$ and $n=30$, SELEX fails when the amplification bias towards non-binders is only about 7% ($Z_B/Z_N \approx 0.93$). Increasing n leads to SELEX failure at even a lesser amplification bias.

According to eq. 1, a single round of partitioning is sufficient for completing binder selection, i.e. reaching $(B/N)_1 \geq 100$, when:

$$(k_N/k_B) \geq 100(N/B)_0 \quad \text{eq. 3}$$

Assuming, in this example, that $k_B \approx 1$, a simple requirement for binder selection is a single round of separation:

$$k_N \leq (B/N)_0/100 \quad \text{eq. 4}$$

Values of $(B/N)_0$ are difficult to estimate for real random sequence oligonucleotide libraries. Rough estimate may be done via binder selection from a DNA library in three consecutive rounds of separation without PCR amplification between them. This estimate, for example, gives $(B/N)_0 \sim 10^{-7}$. According to eq. 4, this estimate suggests $k_N \sim 10^{-9}$ as a rough value which may be sufficient for binder selection in a single round of separation.

All practical separation methods are characterized by $k_N \gg 10^{-9}$ (Ellington et al., In vitro selection of RNA molecules that bind specific ligands. *Nature* 1990, 346, 818-822; Irvine et al., Selexion—systematic evolution of ligands by exponential enrichment with integrated optimization by nonlinear-analysis. *J. Mol. Biol.* 1991, 222, 739-761; Wang et al., Influence of target concentration and background binding on in vitro selection of affinity reagents. *Plos ONE* 2012, 7, e43940). Solid-phase methods (e.g., separation on filters and magnetic beads) are widely used in SELEX, but typically have $k_N > 10^{-3}$ due to non-specific adsorption of non-binders onto the surface and contamination of binders.

Binders from oligonucleotide tagged combinatorial libraries are selected in a process similar to SELEX described above but without PCR amplification of the binders (molecules of non-nucleotide nature cannot be amplified). Owing to the inability to amplify the binders, the number of rounds of selection is typically around 3 or 4; a greater number of rounds leads to the loss of binders. Equations 1 and 2 in this case are modified by replacing $(Z_N/Z_B)^n$ and $(Z_B/Z_N)^n$ with unity.

Capillary electrophoresis (CE) based separation was introduced to exclude the surface as a means of separation of binders from non-binders (Mendonsa et al., In vitro evolution of functional DNA using capillary electrophoresis. *J. Am. Chem. Soc.* 2004, 126, 20-21). Theoretical estimates indicate that $k_N \sim 10^{-9}$ can be achieved in CE-based separation (Kochmann et al., *Predicting efficiency of NECEEM-based partitioning of protein binders from non-binders in DNA-encoded libraries. Electrophoresis* 2018, 39, 2991-2996). However, experiments revealed only $k_N \geq 10^{-5}$, which is two orders of magnitude lower than the lowest $k_N$ of practical solid-phase methods but four orders of magnitude higher than $k_N \sim 10^{-9}$ for completing binders selection in a single round of separation (Berezovski et al., *Nonequilibrium capillary electrophoresis of equilibrium mixtures; a universal tool for development of aptamers. J. Am. Chem. Soc.* 2005, 127, 3165-3171). The main reason for higher than expected $k_N$ of CE-based separation lies in an unusual pattern of oligonucleotide migration in CE (Musheev et al., *Non-uniform Velocity of Homogeneous DNA in a Uniform Electric Field; Consequence of Electric-Field-Induced Slow Dissociation of Highly Stable DNA-Counterion Complexes. J. Am. Chem. Soc.* 2013, 135, 8041-8046). There is a portion of oligonucleotides which tails from the main portion of oligonucleotides. In the context of CE-based separation, there are portions of non-binders that tail towards binders and create non-binder background in the binder-collection time window.

The DNA background (e.g. non-binder background) in CE has several implications. In general, peak shapes depicting concentration profile of the analyte in CE are close to Gaussian (see FIG. 3A) with fast decrease of overlapping analyte concentrations with increasing resolution between the peaks corresponding to the analytes. Until recently, it was generally accepted that DNA in CE has a Gaussian peak shape as well. However, if it were the case, the DNA background in CE-based binder selection from oligonucleotide libraries would be negligibly low having a non-binder transmittance of approximately $k_N \sim 10^{-20}$ to $10^{-100}$ (Kochmann et al. *Predicting efficiency of NECEEM-based partitioning of protein binders from non-binders in DNA-encoded libraries. Electrophoresis* 2018, 39, 2991-2996).

It was discovered that non-binders have a non-Gaussian DNA peak in the publication by Berezovski et al. *Nonequilibrium capillary electrophoresis of equilibrium mixtures; a universal tool for development of aptamers. J. Am. Chem. Soc.* 2005, 127, 3165-3171. The non-Gaussian peak shape was caused by DNA background, equating to a transmittance of $k_N = 10^{-5}$, which was later confirmed with other types of DNA molecules (Drabovich et al. *Selection of smart small-molecule ligands; the proof of principle. Anal. Chem.* 2009, 81, 490-494).

Attempts to decrease the DNA background included increasing the resolution between the peaks of the target-binder complex and non-binders, which were found to be ineffective. The prevailing hypothesis for the nature of the DNA background is the following. Being a linear polyanion, DNA, tightly binds cations such as $Na^+$, $K^+$, $Mg^{2+}$, $Ca^{2+}$, etc. (Musheev et al. *Non-uniform velocity of DNA in a uniform electric field; the consequence of electric-field-induced slow dissociation of highly-stable DNA-counterion complexes. J. Am. Chem. Soc.* 2013, 135, 8041-8046). A part of DNA molecules under thermodynamic equilibrium is bound so strongly to the cation that it co-migrates with the target-binder complex creating the non-binder (DNA) background in binder selection. FIG. 3B below shows the background explicitly with fluorescence detection (even without elaborate qPCR detection).

In other attempts to decrease DNA background, DNA precipitation was found by electrodialysis and which was in turn utilized in an attempt to desalt DNA (Musheev et al. *Stable DNA aggregation by removal of counterions. Anal. Chem.* 2013, 85, 10004-10007). However, it proved to be inefficient as well.

A need, therefore, exists for the development of a method that obviates or mitigates at least one of the disadvantages described above or that provides a useful alternative. For example, there is a need for a method that increases the efficiency of separation for reaching a desired binder-to-non-binder ratio. There is also a need for a method to reduce non-binder background.

The background section is included solely to explain the context of the disclosure. This is not to be taken as an admission that any of the material referred to was published, known, or part of the common general knowledge as of the priority date.

SUMMARY

In accordance with an aspect, there is provided a capillary electrophoresis method comprising: selecting an electroosmotic flow (EOF) in a capillary such that at least one target-binder (TB) complex has a target-binder velocity vector ($v_{TB}$) co-directed with an electric field vector (E) and at least one non-binder (N) has a non-binder velocity vector ($v_N$) in the opposite direction to the electric field vector (E); introducing a sample comprising the at least one target-binder (TB) complex, the at least one non-binder (N), and at least one running buffer into a capillary inlet of the capillary; applying an electric field directed from the capillary inlet to a capillary outlet of the capillary to separate the at least one target-binder (TB) complex from the at least one non-binder (N); and detecting the at least one target-binder complex.

In other aspects, wherein the selected EOF is achieved by adjusting pH and/or ionic strength of the at least one running buffer. In other aspects, wherein the pH is selected such that there is minimal degradation of the at least one target-binder (TB) complex. In other aspects, wherein the pH is about 5 to about 9, about 6 to about 8, or about 6.5 to about 7.5. In other aspects, wherein the at least one running buffer has a pH and/or ionic strength that is similar to physiological pH and/or ionic strength. In other aspects, wherein the EOF is adjusted by increasing or decreasing an ionic strength of the at least one running buffer. In other aspects, wherein the at least one running buffer further comprises at least one salt to modulate the ionic strength of the at least one running buffer. In other aspects, wherein the at least one salt is selected from alkali metal salts, alkaline earth metal salts, or combination thereof. In other aspects, wherein the at least one salt is selected from the group consisting of sodium chloride, sodium iodide, sodium bromide, lithium bromide, lithium iodide, potassium phosphate, sodium bicarbonate, calcium chloride, calcium iodide, calcium bromide, calcium phosphate, calcium bicarbonate, magnesium chloride, magnesium iodide, magnesium bromide, magnesium phosphate, magnesium bicarbonate and a combination thereof. In other aspects, wherein the at least one salt comprises sodium chloride. In other aspects, wherein the concentration of sodium chloride is less than about 1000 mM. In other aspects, wherein the concentration of sodium chloride is about 10 mM to about 200 mM. In other aspects, wherein the ionic strength of the at least one running buffer is within 20% of its physiological value of about 160 mM. In other aspects, wherein increasing the ionic strength of the at least one running buffer leads to an increased temperature in the capillary and the capillary temperature is adjusted by using a simplified universal method for predicting electrolyte temperatures (SUMET). In other aspects, wherein, as the molecular weight of the at least one target of the at least one target-binder complex decreases, the ionic strength is adjusted lower or the pH is adjusted higher to achieve the selected EOF. In other aspects, wherein, as the length of an oligonucleotide of the at least one binder and the at least one non-binder increases, the ionic strength is adjusted lower or the pH is adjusted higher to achieve the selected EOF. In other aspects, wherein separating the at least one target-binder (TB) complex from the at least one non-binder (N) occurs in a single round. In other aspects, wherein the EOF is adjusted so that the equation:

$$(k_N/k_B) \geq 100(N/B)_0 \qquad \text{eq. 3}$$

is satisfied, where $k_N$ is the transmittance for the at least one non-binder, $k_B$ is the transmittance for the at least one binder, and N/B is the at least one non-binder to at least one binder ratio. In other aspects, wherein $k_N$ is less than $1 \times 10^{-6}$. In other aspects, wherein $k_N$ is from about $6 \times 10^{-10}$ to about $8 \times 10^{-6}$. In other aspects, wherein $k_N$ is less than about $6 \times 10^{-10}$. In other aspects, wherein $k_B$ is about 1. In other aspects, wherein $|\mu_N|>|\mu_{EOF}|>|\mu_{TB}|$ is satisfied where $k_N$ is a non-binder mobility vector, $\mu_{EOF}$ is a mobility vector of the electroosmotic flow, and $\mu_{TB}$ is the at least one target-binder complex mobility vector. In other aspects, wherein $|\mu_N|>|\mu_{EOF}|>|\mu_{TB}|$ is satisfied by increasing an ionic strength of the at least one running buffer. In other aspects, wherein the selected EOF is achieved by adjusting pH and/or ionic strength of the at least one running buffer such that $v_{TB}=-v_N$ and $v_{TB}$ is co-directed with E, and EOF mobility vector, $M_{EOF}$, that corresponds to $v_{TB}=-v_N$ is:

$$M_{EOF}=-\tfrac{1}{2}(\mu_N+\mu_{TB}) \qquad \text{eq. 4}$$

$\mu_N$ is $\mu_{DNA}$ and it is about 19 to about 27 mm²/(kVs) $\mu_{TB}$ is calculated from:

$$\mu_{TB} = F(\mu_N, d_T, L_{DNA}) = \frac{d_T^2 \mu_T + (d_{dsDNA} L_{dsDNA} + d_{ssDNA} L_{ssDNA})\mu_N}{d_T^2 + d_{dsDNA} L_{dsDNA} + d_{ssDNA} L_{ssDNA}} \qquad \text{eq. 5}$$

$d_T$ is the diameter of target; $\mu_T$ is the electrophoretic mobility of the target, which is determined by running the target itself in CE along with an EOF marker (neutral molecule): $\mu_T=(v_T-v_{EOF})/E$, where $v_T$ and $v_{EOF}$ are determined by dividing the capillary length, which is from a point where the sample was located at the start time of electrophoresis to a detection point, $l_{cap}$, over the migration times of peaks of the target, $t_T$, and the EOF marker, $t_{EOF}$: $v_T=l_{cap}/t_T$ and $v_{EOF}=l_{cap}/t_{EOF}$; $d_{dsDNA}$ is about 2.6 nm and $d_{ssDNA}$ is about 1.6 nm; for the DNA moiety, the lengths of moieties are calculated by $L_{dsDNA}=b_{dsDNA} \times n_{dsDNA}$, $L_{ssDNA}=b_{ssDNA} \times n_{ssDNA}$, where $b_{dsDNA}=0.34$ nm and $b_{ssDNA}=0.43$ nm are the lengths of dsDNA and ssDNA monomers and $n_{dsDNA}$ and $n_{ssDNA}$ are numbers of nucleotides in all double-stranded regions and all single-stranded regions, respectively; $M_{EOF}$ being calculated and is used for $v_{TB}=-v_N$; the pH and/or $I_{RB}$ of the running buffer is then determined by measuring $\mu_{EOF}$ for a fixed pair of pH and $I_{RB}$ as a starting point and, if $\mu_{EOF}>M_{EOF}$ then $\mu_{EOF}$ is decreased by decreasing pH and/or increasing $I_{RB}$; if $\mu_{EOF}<M_{EOF}$ then $\mu_{EOF}$ is increased by increasing pH and/or decreasing $I_{RB}$.

In other aspects, wherein non-binder background level is reduced compared to a systematic evolution of ligands by exponential enrichment (SELEX) method. In other aspects, wherein the non-binder background level is substantially low. In other aspects, wherein the non-binder background level is lower than the noise of a polymerase chain reaction method.

In other aspects, wherein selecting the EOF reduces non-binder background level. In other aspects, wherein adjusting the EOF reduces non-binder background level detected at the capillary outlet.

In other aspects, further comprising introducing at least one running buffer into the capillary inlet after introducing the sample. In other aspects, wherein the sample and the at least one running buffer are introduced into the capillary via capillary action, pressure, siphoning, or electrokinetically between the capillary inlet and the capillary outlet. In other aspects, wherein the sample and the at least one running buffer are introduced into the capillary by creating a pressure difference between the capillary inlet and the capillary outlet. In other aspects, wherein the sample is propagated from the capillary inlet by the pressure difference before an electric field is applied. In other aspects, wherein the propagation reduces the separation time without having to change the capillary length or the electric field. In other aspects, wherein the at least one binder and the at least one non-binder are selected from oligonucleotide tagged molecules and/or oligonucleotides. In other aspects, wherein an oligonucleotide library comprises the at least one binder and the at least one non-binder. In other aspects, wherein the oligonucleotide library comprises a random-sequence oligonucleotide library. In other aspects, wherein the oligonucleotide library comprises natural (unmodified) oligonucleotides. In other aspects, wherein the oligonucleotide library comprises modified oligonucleotides. In other aspects, wherein the oligonucleotide library comprises a library of oligonucleotide-encoded molecules. In other aspects, wherein the oligonucleotide-encoded molecules comprise DNA-encoded drug-like molecules. In other aspects, wherein the oligonucleotide library comprises aptamers. In other aspects, wherein the oligonucleotide library comprises RNA or single-stranded DNA oligonucleotides. In other aspects, wherein the at least one binder is capable of forming a target-binder complex that has an electrophoretic shift compared to the at least one non-binders. In other aspects, wherein the at least one target is selected from the group comprising proteins, peptides, nucleic acids, amino acids, nucleosides, antibodies, antibody fragments, antibody ligands, peptide nucleic acids, small organic molecules, lipids, hormones, drugs, enzymes, lectin, cell adhesion molecule, antibody epitope, enzyme substrates, enzyme inhibitors, coenzymes, inorganic molecules, carbohydrates, such as polysaccharides and monosaccharides, or a combination thereof. In other aspects, wherein the target is a protein. In other aspects, wherein the at least one binder further comprises a detectable moiety, wherein the detectable moiety is selected from the group consisting of a dye, a quantum dot, a radiolabel, an electrochemical functional group, an enzyme, an enzyme substrate, a ligand and a receptor. In other aspects, wherein the target comprises two or more targets bonded together to provide a greater molecular weight to increase separation of the target-binder complex (es) from the at least one non-binder and the selection of at least one binder for more than one target, simultaneously. In other aspects, wherein the sample comprises an equilibrium mixture having the at least one non-binder and the at least one target-binder complex. In other aspects, wherein the sample is introduced into the capillary as a plug shorter than 10% of the capillary length. In other aspects, wherein the at least one target-binder complex detected is analyzed. In other aspects, wherein the tagging oligonucleotide of the oligonucleotide tagged molecule and/or oligonucleotide is amplified. In other aspects, wherein PCR is used to amplify. In other aspects, wherein detecting the at least one target-binder complex comprises collecting fractions and analyzing the fractions to identify the at least one binder. In other aspects, wherein analyzing comprises using quantitative polymerase chain reaction (qPCR). In other aspects, wherein the results of the qPCR analysis are used to determine the at least one binder distribution among the collected fractions. In other aspects, wherein the electric field is applied by a high voltage power source connected to an anode placed at the capillary inlet and a cathode placed at the capillary outlet. In other aspects, wherein the applied electric field is from about 50 to about 600 V/cm. In other aspects, wherein the detecting of the at least one target-binder complex comprises using a detector. In other aspects, wherein the detector is an optical spectrometer or qPCR. In other aspects, wherein the optical spectrometer comprises a light-absorbance spectrometer or a fluorescence spectrometer. In other aspects, further comprising preparing the sample comprising combining at least one binder, at least one non-binder and at least one target under conditions to form the at least one target-binder complex and the at least one non-binder. In other aspects, further comprises incubating. In other aspects, wherein the at least one target-binder complex has an electrophoretic shift compared to the at least one non-binder. In other aspects, wherein the electroosmotic flow is adjusted so that the target-binder complexes have a velocity of $v_{TB}$ and the non-binders have a velocity of $v_N$ follow: $v_{TB}>0>v_N$.

In other aspects, wherein the capillary is pre-conditioned to provide a stable EOF. In other aspects, wherein a stable EOF has a constant $\mu_{EOF}$ in consecutive CE runs. In other aspects, wherein the capillary is pre-conditioned by a treatment comprising consecutive rinsing. In other aspects, wherein consecutive rinsing comprises rinsing with i) at least one alcohol, ii) at least one acid, iii) at least one base, iv) at least one water, and then v) at least one running buffer, and repeating steps ii) to iv) at least once. In other aspects, wherein further comprising applying voltage with the running buffer.

It is understood that one or more of the aspects described herein (and above) may be combined in any suitable manner. The novel features of the present invention will become apparent to those of skill in the art upon examination of the following detailed description of the invention. It should be understood, however, that the detailed description of the invention and the specific examples presented, while indicating certain aspects of the present invention, are provided for illustration purposes only because various changes and modifications within the spirit and scope of the invention will become apparent to those of skill in the art from the detailed description of the invention and claims that follow.

BRIEF DESCRIPTION OF THE DRAWINGS

The present invention will be further understood from the following description with reference to the figures, in which:

FIG. 8A shows an electropherogram for a CE method using NaCl-free buffer, in which the target-binder complexes and non-binders migrate in the same direction, using fluorescence detection.
FIG. 8B shows an electropherogram for the CE method of FIG. 8A using qPCR detection.

DETAILED DESCRIPTION

Figure 1A:
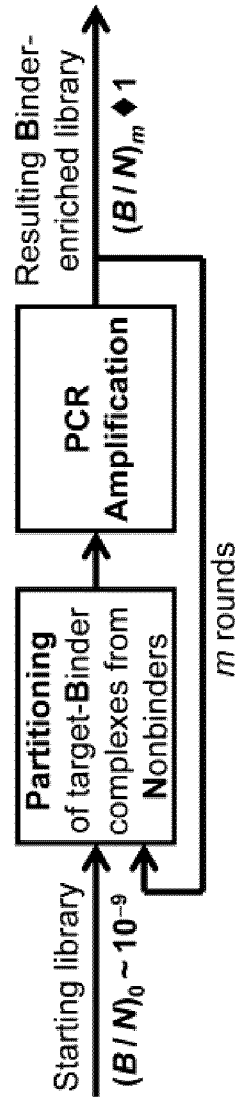
FIG. 1A shows a typical schematic for a SELEX method.
Figure 1B:
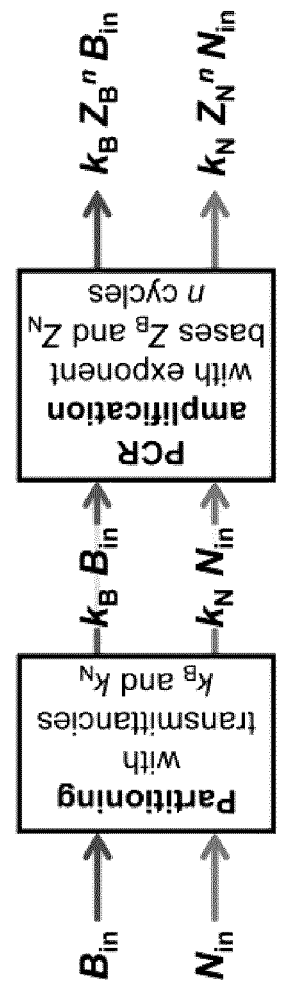
FIG. 1B shows a schematic for a single-round of the SELEX method in FIG. 1A.

In general, there is provided a method of capillary electrophoresis (CE) in which target-binder complex(es) may be separated from non-binder(s). In embodiments, the method facilitates more efficient separation compared to known methods. For example, fewer rounds of separation are provided, typically, one-round separation may be achieved, for example, of a sufficiently pure pool of binders. The methods described herein may be applied to oligonucleotide libraries to select molecules (e.g. binder oligonucleotide tagged molecules (e.g. drugs), and/or oligonucleotides alone, such as aptamers) in the library that have a higher-affinity for a target molecule compared to other molecules (e.g. non-binder oligonucleotide tagged molecules (e.g. drugs), and/or oligonucleotides alone, such as aptamers) in the library, whereby the target-binder complex formed (e.g. the target-bound oligonucleotide tagged molecule and/or oligonucleotide alone) may be separated from the non-binder (e.g. oligonucleotide tagged molecule and/or oligonucleotide alone not bound to the target) for quantitative assessment and/or for further use of such binders in the library, for example, when their structure is revealed, they may be re-synthesized and used in pre-clinical studies for drug development, etc. In embodiments, the separation is provided via movement of the target-binder complex(es) and the non-binder(s) in opposite directions during capillary electrophoresis. In other embodiments, the method reduces background level caused by non-binder(s) to provide better separation of the non-binder from the target-binder complex(es). In certain embodiments, the reduction in the background level caused by non-binder(s) may be orders of magnitude better than in conventional methods.

Definitions

Unless otherwise explained, all technical and scientific terms used herein have the same meaning as commonly understood by one of ordinary skill in the art to which this disclosure belongs. Although any methods and materials similar or equivalent to those described herein can be used in the practice for testing the present invention, the typical materials and methods are described herein. In describing and claiming the present invention, the following terminology will be used.

It is also to be understood that the terminology used herein is for the purpose of describing particular aspects only and is not intended to be limiting. Patent applications, patents, and publications are cited herein to assist in understanding the aspects described. All such references cited herein are incorporated herein by reference in their entirety and for all purposes to the same extent as if each individual publication or patent or patent application was specifically and individually indicated to be incorporated by reference in its entirety for all purposes. To the extent publications and patents or patent applications incorporated by reference contradict the disclosure contained in the specification, the specification is intended to supersede and/or take precedence over any such contradictory material.

In understanding the scope of the present application, the articles "a", "an", "the", and "said" are intended to mean that there are one or more of the elements. Additionally, the term "comprising" and its derivatives, as used herein, are intended to be open ended terms that specify the presence of the stated features, elements, components, groups, integers, and/or steps, but do not exclude the presence of other unstated features, elements, components, groups, integers and/or steps. The foregoing also applies to words having similar meanings such as the terms, "including", "having" and their derivatives.

It will be understood that any aspects described as "comprising" certain components may also "consist of" or "consist essentially of," wherein "consisting of" has a closed-ended or restrictive meaning and "consisting essentially of" means including the components specified but excluding other components except for materials present as impurities, unavoidable materials present as a result of processes used to provide the components, and components added for a purpose other than achieving the technical effect of the invention. For example, a composition defined using the phrase "consisting essentially of" encompasses any known acceptable additive, excipient, diluent, carrier, and the like. Typically, a composition consisting essentially of a set of components will comprise less than 5% by weight, typically less than 3% by weight, more typically less than 1%, and even more typically less than 0.1% by weight of non-specified component(s).

It will be understood that any component defined herein as being included may be explicitly excluded from the claimed invention by way of proviso or negative limitation.

In addition, all ranges given herein include the end of the ranges and also any intermediate range points, whether explicitly stated or not.

Terms of degree such as "substantially", "about" and "approximately" as used herein mean a reasonable amount of deviation of the modified term such that the end result is not significantly changed. These terms of degree should be construed as including a deviation of at least ±5% of the modified term if this deviation would not negate the meaning of the word it modifies.

The abbreviation, "e.g." is derived from the Latin exempli gratia, and is used herein to indicate a non-limiting example. Thus, the abbreviation "e.g." is synonymous with the term "for example." The word "or" is intended to include "and" unless the context clearly indicates otherwise.

It is further to be understood that all molecular weight or molecular mass values, are approximate and are provided for description. Although methods and materials similar or equivalent to those described herein can be used in the practice or testing of this disclosure, suitable methods and materials are described below.

As used herein, the terms "separating" and the like, and "partitioning" and the like, are used interchangeably.

As used herein, the term "oligonucleotide library" and the like refers to a library of molecules that comprise oligonucleotide tagged combinatorial libraries, such as oligonucleotide tagged molecules (e.g. oligonucleotide tagged drugs), and/or oligonucleotides alone, such as aptamers. The oligonucleotide libraries of molecules may bind target molecules with selectivity and specificity. The oligonucleotide libraries of molecules encompass, for example, random-sequence oligonucleotide libraries, natural (unmodified) oligonucleotide libraries, modified oligonucleotide libraries, oligonucleotide-encoded libraries, and DNA-encoded drug-like libraries.

As used herein the term "oligonucleotides" and the like as used herein refer to a linear nucleic acid (e.g. may be any natural or synthetic nucleic acids) molecule (such as DNA or RNA) sequence of at least 2 nucleotides, for example, at least 3 nucleotides, at least 5 nucleotides, at least 9, at least 15, at least 18, at least 24, at least 30, at least 50, at least 100, at least 200 or even at least 500 nucleotides long. However shorter or longer oligonucleotides may be used. Oligonucleotides may be designed to have different lengths. The oligonucleotides may be single stranded or double stranded, as specified, or contain portions of both double stranded or single stranded sequence. The oligonucleotide may be aptamers, DNA, RNA or a hybrid, where the nucleic acid contains any combination of deoxyribo- and ribo-nucleotides, and any combination of bases, including uracil, adenine, thymine, cytosine, guanine, inosine, xathanine hypoxathanine, isocytosine, isoguanine, etc. Oligonucleotides can be formed from chemically modified DNA or RNA nucleotides.

As used herein the term "oligonucleotide tagged molecules" and the like as used herein refers to any suitable oligonucleotide covalently bonded to a molecule. The "molecule" is understood to be any suitable compounds/molecules. In some embodiments, the molecule can be an enzyme substrate, a ligand, an antagonist, and any other applicable reactant that can bond to oligonucleotide(s). In some embodiments, the molecule is a therapeutic agent. In some embodiments, the molecule is a therapeutic candidate. The molecule may be a basic, acidic and/or neutral drug. Examples include alpha-blockers, such as Nicergoline or Prazosin; anesthetics/analgesics, such as Alfentanil, Ketamine or Ethidocaine; analgetics, such as Fentanil, Meperidine, Methadone or Phenylbutazone; anesthetics, such as Bupivacaine, Etidocaine or Phencyclidine; anesthetics/antiarrhytmics, such as Lidocaine or Phencyclidin; antiarrhytmics, such as Aprindine, Disopyramide, Quinidine or Verapamil; antibiotics, such as Erythromycin; anticoagulants, such as Acenocoumarol, Dipyridamole, PCR2362 (thieno-pyridine derivative), Ticlopidine or Warfarin; antiepileptics, such as Phenytoin or Carbamazepine; antiinflammatory agents, such as Naproxen; beta-blockers, such as Alprenolol, Metoprolol, Oxprenolol, Pindolol and related compounds, Propranolol or Timolol; steroids, such as Progesterone, Cortexone, Cortisol, Testosteron, Estradiol or Prednisolone; neuromuscular blockers, such as Metocurine or d-Tubocurarine; psychotropics, such as Amitriptyline, Chlorpromazine, Cyclazindol, Desmethylimipramine, Diazepam, Doxepine, Flurazepam, Fluphenazine, Haloperidol, Imipramine, Loxapine, Mianserin, Nortriptyline, Norzimelidine, Perazine, Perphenazine, Phenobarbital, Phenothiazine derivatives, Promazine, Acepromazine, Protipendyl, Thioridazine, Thiothixene, Triazolam, Trifluoperazine orZimelidine; vitamins and provitamins, such as Vitamin $B_{12}$ or folic acid; further drugs, such as Aminopyrine, Amoxapine, Bupropion, Maprolitine, Nomifensine, Trazodone, drugs with quaternary ammonium group, Ritodrine, Doxazosin, Trimazosin, Binedalin, Amsacrine, Apazone, SKF 525A, Ciclazindol, PCR 2362, Indomethacin, Probenecid, Retinoic Acid, Sulfinpyrazone, Tolmetin, Benoxaprofen, Heparin, Sufentanil, Lofentanil, Metoclopramide, Nicardipine, Pirmenol, mifepristone, RU 42 633, Aprindil, Auramine O, Bepridil, Desipramine, Desmethylclomipraine, Moxaprindine, Quinine, Lorcainide, Prothipendyl, Protriptyline, Trihexyphenidyl, Biperiden, Methaqualone, Diphenhydramine, Glutethimide, Chlordiazepoxid, L-Tryptophane, Mepivacaine, Levomethadone, Opipramol, Trifluopromazine orTrimipramine; plasticicers, such as tris-butoxyethyl phosphate (TBEP); staurosporine or staurosporine derivatives, such as N-benzoyl-staurosporine or 7-hydroxy staurosporine, as well as a metabolite of any of these compounds; pharmaceutically acceptable salt thereof. The oligonucleotide tagged molecules may have high specificity and affinity for their associated targets and may offer unique chemical and biological characteristics in terms of biochemical activity, molecular recognition or binding attributes.

The term "aptamer" refers to a class of nucleic acids that are composed of RNA or single-stranded DNA oligonucleotides and may have high specificity and affinity for their associated targets and may offer unique chemical and biological characteristics in terms of biochemical activity, molecular recognition or binding attributes. Usually, an aptamer has a molecular activity such as binding to a target molecule at a specific epitope (region).

A used herein, the term "target molecule" or "target" can be used interchangeably, and includes any suitable compound/molecule upon which a binder can act in a desirable manner (e.g., binding of the target, catalytically changing the target, reacting with the target in a way that modifies or alters the target or the functional activity of the target, covalently attaching to the target (as in a suicide inhibitor)) to provide a target-binder complex that has an electrophoretic shift compared to the non-binders. Target molecules can include, without limitation, proteins, peptides, nucleic acids, amino acids, nucleosides, antibodies, antibody fragments, antibody ligands, peptide nucleic acids, small organic molecules, lipids, hormones, drugs, enzymes, lectin, cell adhesion molecule, antibody epitope, enzyme substrates, enzyme inhibitors, coenzymes, inorganic molecules, carbohydrates, such as polysaccharides and monosaccharides. Virtually any chemical or biological effector may be a suitable target. Molecules of any size can serve as targets. A target can also be modified in certain ways to enhance the likelihood or strength of an interaction between the target and the binder. A target may also include any minor variation of a particular compound or molecule, such as, in the case of a protein, for example, variations in its amino acid sequence, disulfide bond formation, glycosylation, lipidation, acetylation, phosphorylation, or any other manipulation or modification, such as conjugation with a labeling component, which does not substantially alter the identity of the molecule.

As used herein, the term "polypeptide" (used interchangeably with "protein" with the understanding that "polypeptide" is broader in scope) includes a molecule having a sequence of amino acids linked by peptide bonds. This term includes proteins, fusion proteins, oligopeptides, cyclic peptides, and polypeptide derivatives. The protein can include antibodies, enzymes, ligand receptors, and any other type of polypeptides having functional characteristics. The polypeptide can be in its natural conformation or have an altered conformation. It is typically a polymer of at least three amino acids, linked to one another by peptide bonds. In some embodiments, the term is used to refer to specific functional classes of polypeptides, such as, for example, receptors, enzymes, signaling proteins, structural proteins, autoantigen polypeptides, nicotinic acetylcholine receptor polypeptides, alloantigen polypeptides, etc. For each such class, there are several examples of amino acid sequences of known exemplary polypeptides within the class; in some embodiments, such known polypeptides are reference polypeptides for the class. In some instances, the polypeptide encoded is smaller than about 50 amino acids and the polypeptide is then termed a peptide. If the polypeptide is a peptide, it will be at least about 2, 3, 4, or at least 5 amino acid residues long. Thus, polypeptides include gene products, naturally occurring polypeptides, synthetic polypeptides, homologs, orthologs, paralogs, fragments and other equivalents, variants, and analogs of the foregoing. A polypeptide may be a single molecule or may be a multi-molecular complex such as a dimer, trimer, or tetramer. They may also comprise single chain or multichain polypeptides such as antibodies or insulin and may be associated or linked. Most commonly disulfide linkages are found in multichain polypeptides. The term polypeptide may also apply to amino acid polymers in which one or more amino acid residues are an artificial chemical analogue of a corresponding naturally occurring amino acid.

A polypeptide may have from about 10 to about 1000 amino acid residues and, even more typically from about 20 to about 500 amino residues. Thus, as used herein, a polypeptide includes what is often referred to in the art as an oligopeptide (5-10 amino acid residues), a polypeptide (11-100 amino acid residues) and a protein (>100 amino acid residues). A polypeptide encoded by an encoding region can undergo post-translational modification to form conjugates with carbohydrates, lipids, nucleic acids and the like to form glycopolypeptides (e.g., glycoproteins), lipopolypeptides (e.g. lipoproteins) and other like conjugates.

Examples of polypeptides include insulin for the treatment of diabetes, interferon for treating viral infections, interleukins for modulating the immune system, erythropoietin for stimulating red blood cell formation, and growth factors that act to mediate both prenatal and postnatal growth. Carrier polypeptides include β-galactosidase, glutathione-S-transferase, the N-terminus of L-ribulokinase, bacteriophage T4 gp55 protein, and bacterial ketosteroid isomerase protein. An example includes α1-acid glycoprotein (AGP).

As used herein, the term "binder" means any compound/molecule that has selective binding affinity for a target molecule. For example, the binder includes oligonucleotide tagged molecules (e.g. oligonucleotide tagged drugs), and/or oligonucleotides alone, such as aptamers. The binder has, for example, a high specificity and affinity for their associated targets and may offer unique chemical and biological characteristics in terms of biochemical activity, molecular recognition or binding attributes. Target(s) may be combined with a random-sequence oligonucleotide library, whereby the target(s) are permitted to react with the binders in the library such that binding occurs between the target(s) and binders, forming target-binder complexes. In embodiments, wherein a binder may further comprise a detectable moiety, wherein the detectable moiety is selected from a dye, a quantum dot, a radiolabel, an electrochemical functional group, an enzyme, an enzyme substrate, a ligand, or a receptor.

As used herein, the term "non-binder" means any compound/molecule that does not bind to a target molecule. For example, the non-binder includes oligonucleotide tagged molecules (e.g. oligonucleotide tagged drugs), and/or oligonucleotides alone, such as aptamers. Target(s) may be combined with a random-sequence oligonucleotide library, whereby the target(s) are permitted to react with the binders and non-binders in the library such that binding does not occur between the target(s) and non-binders. Binders that dissociate from their target-binder complexes during the method may be considered non-binders.

As used herein, the term "target-binder complex" is, for example, a complex formed from an interaction between a target and a binder (e.g., binding of the target, catalytically changing the target, reacting with the target in a way that modifies or alters the target or the functional activity of the target, covalently attaching to the target (as in a suicide inhibitor), or non-covalently attaching to the target). Interactions between the target and binder may include, for example, three-dimensional, shape-dependent interactions as well as hydrophobic or electrostatic interactions, base-stacking, and intercalation. The target-binder complex has an electrophoretic mobility that is different from the electrophoretic mobility of the non-binder(s). In other embodiments, two or more targets may be linked (e.g. bonded) to have a greater molecular weight to assist in separation of the target-binder complex(es) from the non-binders and the selection of binders for more than one target simultaneously. The linked targets may be small-molecule(s) that may, for example, form protein(s).

As used herein, the term "electrophoresis" is understood to mean, for example, the electrokinetic separation methods performed in submillimeter inner diameter capillaries and in microfluidic and nanofluidic channels. With respect to capillary electrophoresis (CE), CE is an analytical technique that separates ions based on differences in their electrophoretic mobility with the use of a voltage applied to the ends of the capillary. The electrophoretic mobility is dependent upon, for example, the effective charge of the molecule and its friction coefficient which depends on the size of the molecule and the viscosity of the running buffer. The velocity at which a charged particle moves is directly proportional to the applied electric field—the greater the field strength, the faster the movement. CE may include the separation of one or more molecules from other molecules in a sample, based on their electrophoretic mobility while being exposed to an electric field. (Li, Sam. Capillary Electrophoresis: Principles, Practice, and Applications. Journal of Chromatography Library; Elsevier Science Publishers: The Netherlands, 1992; Vol 52).

As used herein, the terms "capillary tube" and "capillary" is used broadly herein to denote any open channel having opposite open ends (i.e., an inlet and outlet) such that fluid can be passed through the length of the channel. The capillary can, for example, include any hollow tube, as well as any channel, column, conduit, passage, etc., that permits the flow of a liquid, typically under specified conditions (e.g., of temperature, pressure, etc.). The capillary may comprise any suitable material known to those skilled in the art for CE. For example, glass, Teflon or any other typical material. The capillary tube of the methods described herein may have any suitable length and diameter. The capillary tube has at least two ends (i.e., an inlet and outlet). In some embodiments the channel is round (tubular), the cross section is generally circular, and the cross-sectional area is simply the area of the circle defined by the channel cross section (area=$\pi r^2$). For example, the capillaries have sub-millimeter diameter.

Lengths can include lengths greater than 5 cm, and typically from about 1 cm to about 300 cm. In some embodiments, the capillary is an individual stretch of conventional capillary tubing. The passageways can have linear or non-linear central axes, e.g., they can be coiled, curved or straight. The cross-sectional geometry of the passageway is not critical, so long as it allows the channel to function as an extraction channel. For example, capillary tubes having a round cross-sectional geometry work well and can be purchased from a number of vendors. However, other geometries, such as oval, rectangular or another polygonal shape, or a combination of such shapes, can also be employed. The structure and configuration of the capillary can assume any of a wide variety of configurations. The capillary can be provided as a single capillary or multiple capillaries linked, for example, in sequence or a bundle of capillaries. In embodiments, the capillary can be made of fused silica and coated with a flexible coating material on the outer surface, typically polyimide or another polymer or resin. Typical coating materials include non-conductive coatings such as polyimide, silicone, polyacrylate, fluoropolymer, polystyrene, polymethylmethacrylate, fluoroplastic, and acrylic. In other embodiments, wherein the inner surface of the capillary is coated with a cationic layer or an anionic layer.

A capillary, or capillary tube, may be considered a microreactor. If analysis requires a chemical reaction, e.g. labeling followed by separation in a capillary, the reaction can be done inside the capillary with very small volumes of reactants for analytical applications. Reactions in the capillary can be carried out in nanoliter volumes. In addition, the capillary can be easily interfaced with optical, qPCR, electrochemical, and mass-spectrometric detectors, thereby offering analytical capabilities. It is known in the relevant art that a particular volume of liquid introduced into a capillary may be referred to as a "plug". Accordingly, in the methods and system described herein, fluids may be introduced into the capillary as a suitable plug of fluid such that, for example, without substantially affecting the non-binder background. In some embodiments, a sample is introduced into the capillary as a plug shorter than about 10% of the capillary length.

As used herein, the term "electroosmotic flow (EOF)" is the motion of liquid induced by an applied potential across a porous material, capillary tube, membrane, microchannel, or any other fluid conduit. EOF is inherent in electrophoresis applications.

As used herein, the terms "oligonucleotide background" or "non-binder background" or "DNA background" are understood to be the transmittance of non-binders that tail towards a target-binder complex, for example, during CE-based separation (e.g. partitioning) of target-binder complexes from non-binders.

As used herein, the term "equilibrium mixture" is understood to include an equilibrium mixture of binder(s), non-binder(s), target molecule(s), and target-binder complex(es).

As used herein, the term "buffer" or "running buffer" is understood to include a suitable pH-buffering solution having an ionic strength that may exceed the ionic strength of the sample and that is used in an electrophoretic separation process. In an exemplary embodiment, a sample containing a mixture of binder(s), non-binder(s), and target-binder complex(es) is added to a running buffer and injected into the capillary. The running buffer is any suitable buffer for CE. Examples of suitable buffers include, but are not limited to, tris-HCl, tris-acetate, etc. In an exemplary embodiment, the running buffer contains a weak base. Examples of suitable weak bases include, but are not limited to, arginine, lysine, histidine, and tris. The running buffer typically has a pH, for example, in the range of about 5 to about 9. The types of buffer in the running buffer include, but are not limited to, morpholinoethanesulfonic acid (MES), N-(2-acetamido)iminodiacetic acid (ADA), N-(2-acetamido)-2-aminoethanesulfonic acid (ACES), N,N-bis(2-hydroxyethyl)-2-aminoethanesulfonic acid (BES), 3-morpholinopropanesulfonic acid (MOPS), N-tris(hydroxymethyl)methyl-2-aminoethanesulfonic acid (TES) and 2-[4-(2-hydroxyethyl)-1-piperazinyl]ethanesulfonic acid (HEPES).

As used herein, the term "salt" is understood to include any suitable salt for combining with a buffer to adjust its ionic strength. A salt is any compound produced by the interaction of an acid and a base. Exemplary salts include, but are not limited thereto, alkali and alkaline earth metal salts (e.g. sodium chloride, sodium iodide, sodium bromide, lithium bromide, lithium iodide, potassium phosphate, sodium bicarbonate, calcium chloride, calcium iodide, calcium bromide, calcium phosphate, calcium bicarbonate, magnesium chloride, magnesium iodide, magnesium bromide, magnesium phosphate, magnesium bicarbonate and the like). In water and other aqueous solutions, salts typically dissociate into an "anion" or negatively charged subcomponent, and a "cation" or positively charge subcomponent. For example, when sodium chloride (NaCl) is dissolved in water, it dissociates into a sodium cation and a chloride anion. Exemplary salts are discussed, e.g., in Waser, Jurg, Quantitative Chemistry, A Laboratory Text, W. A. Benjamin, Inc., New York, page 160, (1966).

Binder Selection

In embodiments, target-binder complex(es) are separated from non-binders using CE. In a typical embodiment, oligonucleotide tagged molecules (e.g. oligonucleotide tagged drugs), and/or oligonucleotides alone are negatively charged. The oligonucleotide tagged molecules and/or oligonucleotides alone are exposed to one or more targets. At least one of the oligonucleotide tagged molecules and/or oligonucleotides alone form a complex with the target(s) referred to as a target-binder complex(es). The ones that do not bind to the target are referred to as non-binders. The non-binders may be characterized by a value of electrophoretic mobility, $\mu_N$, which is negative, i.e. vector $\mu_N$ has an opposite direction to the vector of the electric field E. In other embodiments, the oligonucleotide tagged molecules and/or oligonucleotides alone are provided from an oligonucleotide library (e.g. several oligonucleotide tagged molecules (e.g. oligonucleotide tagged drugs), and/or oligonucleotides alone.

In a specific embodiment, an aptamer library (e.g. oligonucleotides alone) is provided. One or more of the aptamers of the library are negatively charged. The library is exposed to one or more targets. At least one of the aptamers form a complex with the target(s) and form a target-aptamer binder complex(es). The aptamers that do not bind to the target are, again, referred to as non-binders. The non-binders may be characterized by a value of electrophoretic mobility, $\mu_N$, which is negative, i.e. vector $\mu_N$ has an opposite direction to the vector of the electric field E.

In an example, typical targets (e.g. proteins) are selected to provide an electrophoretic shift when bound to a binder (e.g. oligonucleotide tagged molecules (e.g. oligonucleotide tagged drugs), and/or oligonucleotides alone (e.g. aptamers)). It is unlikely that the protein has a positive charge of a magnitude greater than the negative charge of the binder to make the complex positively charged. Accordingly, the target-binder complexes (for a single target) have a negative charge that may be characterized by a single value of negative electrophoretic mobility $\mu_{TB}$, i.e. the vector $\mu_{TB}$ is co-directed with the vector $\mu_N$ and both of them are opposite in direction to the vector of the electric field E. The hydrodynamic size of the target-binder complex is greater than that of the non-binder. Thus, target-binder complexes typically have a greater drag force in electrophoresis than non-binders. As a result, the magnitude of electrophoretic mobility of target-binder complexes is lower than that of non-binders: $|\mu_{TB}| < |\mu_N|$.

Figure 2A:
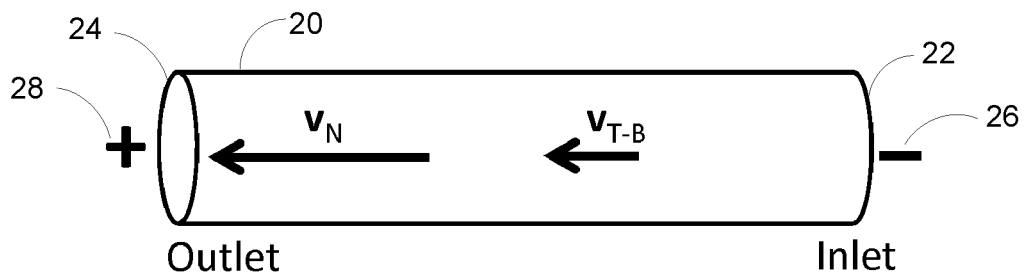
FIG. 2A shows a view of velocity vectors through a capillary during standard capillary electrophoresis (CE).
Figure 2B:
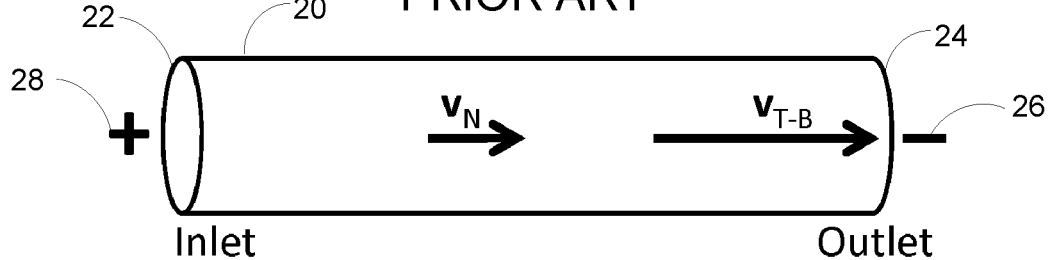
FIG. 2B shows a view of the velocity vectors through a capillary during standard CE with the polarity reversed compared to FIG. 2A.

Two known modes of CE-based separation differ by polarity, but in both, non-binders and target-binder complexes move in the same direction as shown in FIGS. 2A and 2B, (Berezovski et al., *Nonequilibrium capillary electrophoresis of equilibrium mixtures; a universal tool for development of aptamers.* J. Am. Chem. Soc. 2005, 127, 3165-71; Mendonsa, et al., *In vitro selection of high-affinity DNA ligands for human IgE using capillary electrophoresis.* Anal. Chem. 2004, 76, 5387-5392). FIGS. 2A and 2B show movement of target-binder complexes and non-binders through a capillary 20 during standard CE-based partition with velocity vectors of target-binder complexes and non-binders directed from capillary inlet 22 towards capillary outlet 24, biased at negative 26 and positive 28 polarities, respectively. Separating target-binders complexes from non-binders is usually realized by selecting a cut-off time for separation.

Figure 2C:
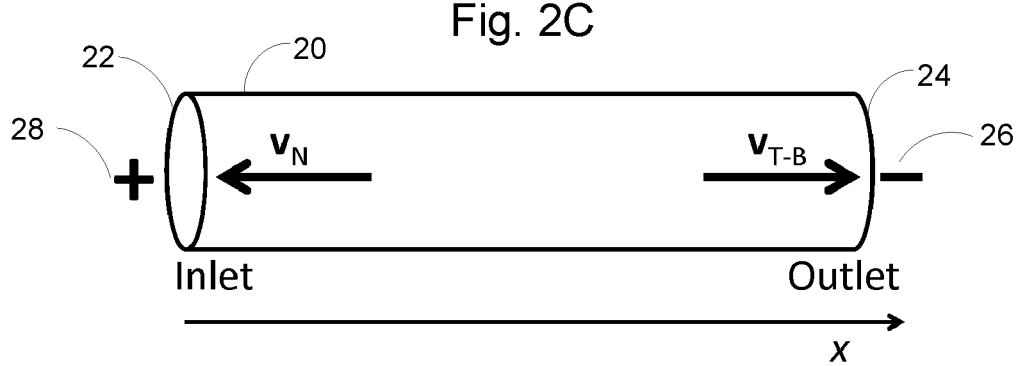
FIG. 2C shows a view of the velocity vectors through a capillary during an embodiment of the CE method.
Figure 3A:
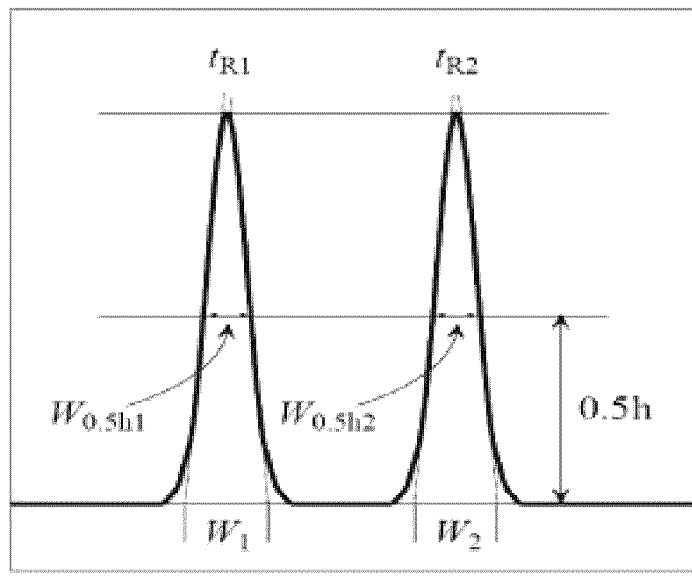
FIG. 3A shows typical Gaussian-shaped peaks in CE, which are resolved to the baseline and have negligible overlap.
Figure 3B:
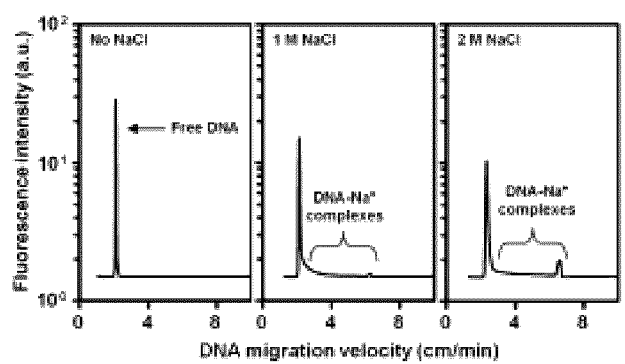
FIG. 3B shows a dependence of DNA velocity in a uniform electric field, depicting increased non-uniformity of this velocity from the case with no NaCl (left) to the case with about 1 mM NaCl (middle) to the case with about 2 mM NaCl (right).

In CE-based separation, $k_N$ (transmittance of separation for non-binders) may be significantly decreased if the target-binder complexes and non-binders moved in the opposite directions, as shown in FIG. 2C, such that irregularly moving non-binders, which constitute the non-binder background, may be prevented from exiting the capillary outlet 24 for a time sufficient for the target-binder complexes to exit. This contradicted the fundamental teachings in (Musheev et al., *Non-uniform Velocity of Homogeneous DNA in a Uniform Electric Field; Consequence of Electric-Field-Induced Slow Dissociation of Highly Stable DNA-Counterion Complexes.* J. Am. Chem. Soc. 2013, 135, 8041-8046). The efficiency of separation is equal to $k_B/k_N$; $k_B \sim 1$, wherein $k_B$ is transmittance of separation for binders; therefore increasing $k_B/k_N$ can be done by reducing non-binder background (decreasing $k_N$). With respect to the non-binder background, the method reduces the background caused by non-binder(s) (e.g. quantity) to provide better separation of the non-binder from the target-binder complex(es). In certain embodiments, the reduction in the background caused by non-binder(s) may be orders of magnitude better than in conventional methods. For example, the non-binder background is substantially low (e.g. below the noise of PCR). More than one consecutive round of selection may be used for selection of aptamers so that the abundances of different sequences (e.g. after using new-generation DNA sequencing) is used to rank the quality (e.g. affinity to the target) of the selected binders.

In an example in FIG. 2C, a one-dimensional system of coordinates with axis x is co-directed with electric field vector E. In this example of CE, $v_{TB}$ is in the same direction as E and the axis x and $v_{TB} > 0$, and $v_N$ is opposite in direction to E and the axis x and $v_N < 0$. These velocities depend on E as well as on $\mu_{TB}$, $\mu_N$, and the mobility vector of electroosmotic flow (EOF), $\mu_{EOF}$. These dependencies are scalar products of vector E and sums of the corresponding mobility vectors:

$$v_{TB} = E(\mu_{EOF} + \mu_{TB}) \text{ and } v_N = E(\mu_{EOF} + \mu_N) \qquad \text{eq. 6}$$

E and $\mu_{EOF}$ are in the same direction except for pH values of the buffer less than 1, which are too extreme for biological native conformation of biological molecules. For instance, typical conditions used for the partitioning mode shown in FIG. 2B are higher than physiological pH and lower than physiological ionic strength of buffer, $I_{RB}$. For example, such conditions may be pH 8.3 and $I_{RB} = 50$ mM. These conditions result in $|\mu_{EOF}| > |\mu_N| > |\mu_{TB}|$ which, in turn, leads to undesirable $v_{TB} > v_N > 0$ as shown in FIG. 2B. The relation $v_{TB} > 0 > v_N$ may be achieved by decreasing $|\mu_{EOF}|$ to satisfy $|\mu_N| > |\mu_{EOF}| > |\mu_{TB}|$. Decreasing $|\mu_{EOF}|$ may be possible by decreasing the zeta potential of the negatively-charged surface of the inner wall of a fused silica capillary via either coating the surface with a neutral layer or increasing $I_{RB}$ (Lipponen et al., *Stable neutral double hydrophilic block copolymer capillary coating for capillary electrophoretic separations.* Electrophoresis 2014, 35, 1106-1113; Melanson et al., *Dynamic capillary coatings for electroosmotic flow control in capillary electrophoresis.* Trends Anal. Chem. 2001, 20, 365-374; Weiliang et al., *Capillary electrophoresis of anions at high salt concentrations.* Electrophoresis 1998, 19, 2133-2139).

In embodiments, coating the inner surface of the capillary 20 typically changes EOF from strong to weak resulting in $|\mu_N| > |\mu_{TB}| > |\mu_{EOF}|$ and, which in turn results in $v_N < v_{TB} < 0$, as shown in FIG. 2A. In contrast, gradually increasing $I_{RB}$ can gradually change $\mu_{EOF}$, potentially reaching $|\mu_N| > |\mu_{EOF}| > |\mu_{TB}|$. However, increasing $I_{RB}$ leads to greater Joule heat generation and increased temperature inside the capillary, $T_{cap}$, which may lead to dissociation of target-binder complexes (Evenhuis et al., *Universal method for determining electrolyte temperatures in capillary electrophoresis.* Anal. Chem. 2011, 83, 1808-1814). The increased temperature can be addressed by using a simplified universal method for predicting electrolyte temperatures (SUMET) which allows adjusting $T_{cap}$ to a desirable value by rationally lowering the electric field strength, E (Patel et al., *Simplified universal method for determining electrolyte temperatures in a capillary electrophoresis instrument with forced-air cooling.* Electrophoresis 2012, 33, 1079-1085). Increasing $I_{RB}$ makes the buffer resemble a buffer with physiological ionic strength and permits the selection of binders intended for use in vivo (e.g., as detection probes, drugs, or drug-delivery vehicles) such that the target-binder complex formed is less likely to dissociate.

Figure 4:
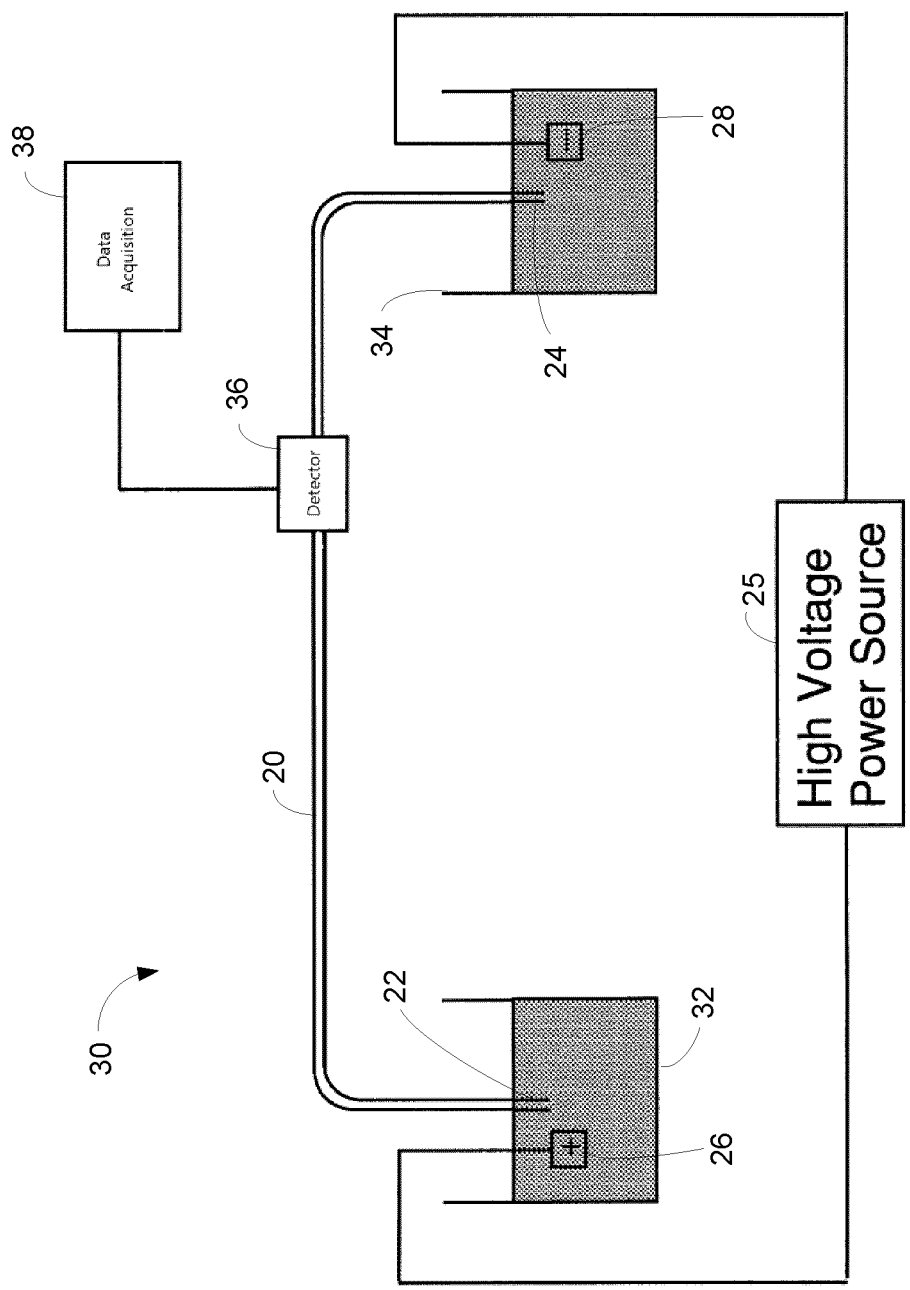
FIG. 4 shows a simplistic schematic drawing of an apparatus that may be used during an embodiment of the CE method.

An exemplary schematic of a simplified version of a capillary electrophoresis system 30 is shown in FIG. 4. Typically, the system further includes a temperature-stabilization system for the capillary, a cooling garage for the sample storage, fraction collection robotics, etc. A commercial system such as a P/ACE MDQ™ apparatus (SCIEX, Concord, ON, Canada) equipped with a laser-induced fluorescence (LIF) detection system is an example of such a CE system used. Such CE systems may be used to perform a method to achieve the results of FIG. 2C. A capillary 20 having a capillary inlet 22 and a capillary outlet 24. Capillary inlet 22 is initially placed in a sample inlet reservoir 32 in which an anode 26 is placed. The sample having a target-binder(s) complex and non-binder(s) and at least one buffer. A cathode 28 is placed in an outlet reservoir 34. Outlet reservoir 34 is typically filled with buffer. A high voltage power source 25 connected to the anode 26 and cathode 28 is used to apply an electric field E across the capillary 20 with a direction from the capillary inlet 22 to the capillary outlet 24. Before the capillary outlet 24, a detector 36 is capable of detecting the target-binder complexes in the capillary 20. The detector 36 may be connected to a data acquisition 38 apparatus such as, but not limited to, a controller or a computer. Detector(s) 36 that may be used in this system are, but not limited to, a mass spectrometer, an optical spectrometer, a light-absorbance spectrometer, or a fluorescence spectrometer. Fractions may also be collected from the capillary and the tagging oligonucleotide of the oligonucleotide tagged molecule and/or oligonucleotide alone is amplified using, for example, PCR (e.g. off-line" quantitative polymerase chain reaction (qPCR) detection). This type of detection may be used when the concentration of target-binder complexes is below the lower limit of detection of on-line detectors. The tagging oligonucleotide is sequenced and the structure of at least one molecule of the oligonucleotide tagged molecule and/or the sequence of the oligonucleotide alone which binds to the target may be determined.

Figure 5:
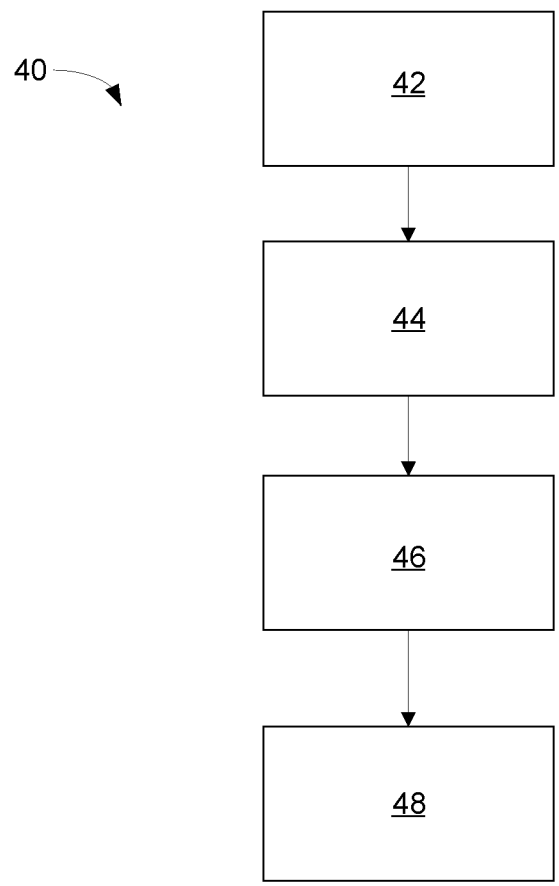
FIG. 5 shows a flow chart depicting an embodiment of the CE method.

FIG. 5 shows a flow diagram depicting a method of CE, generally referred to by the number 40. In 42, an electroosmotic flow (EOF) in a capillary such that (i) at least one target-binder complex has a target-binder velocity vector ($v_{TB}$) co-directed with an electric field vector (E) and at least one non-binder (N) has a non-binder velocity vector ($v_N$) in the opposite direction to the electric field vector (E) and (ii) the non-binder background level is reduced in the region of migration of the at least one target-binder complex to a level such that the amount of target-binder complexes is greater than that of non-binder background level. In 44, the sample comprising the at least one target-binder complex, the at least one non-binder (N), and the at least one running buffer, is introduced into the capillary inlet (optionally followed by introduction of the at least one running buffer (or a different buffer)). In 46, an electric field directed from the capillary inlet to the capillary outlet is applied for separating the at least one target-binder complex from the at least one non-binder. In 48, detecting the at least one target-binder complex.

In another embodiment, in 42, the electroosmotic flow (EOF) is selected by adjusting at least one of pH and ionic strength of the at least one running buffer. In 44, the sample, having the at least one running buffer, is introduced into the capillary inlet 22 by placing the capillary inlet into the reservoir 32 containing the sample and the at least one running buffer (optionally placing the capillary inlet into a reservoir (not shown) containing the at least one running buffer (or a different buffer)). The sample and the at least one running buffer is introduced, for example, via capillary action, pressure, siphoning, or electrokinetically between the capillary inlet 22 and capillary outlet 24. In typical embodiments, the sample and the at least one running buffer is introduced via pressure. The sample may be introduced into the capillary 20 by creating a pressure difference between the capillary inlet 22 and the capillary outlet 24. This pressure difference may be achieved by a pump, such as a syringe pump. In 46, the electric field is applied with its vector E being directed from the capillary inlet 22 to the capillary outlet 24 (i.e., positive polarity being at the capillary inlet and negative polarity being at the capillary outlet). In 48, the target-binder complexes are detected at the capillary outlet 24, which are substantially separated from the non-binder(s).

In a further embodiment, in 42, the electroosmotic flow (EOF) is selected by adjusting at least one of pH and ionic strength of the at least one running buffer. In 44, the sample, having the at least one running buffer, is introduced into the capillary inlet 22 by placing the capillary inlet into the reservoir 32 containing the sample and the at least one running buffer. The sample and the at least one running buffer is introduced, for example, via capillary action, pressure, siphoning, or electrokinetically between the capillary inlet 22 and capillary outlet 24. In 46, the electric field is applied with its vector E being directed from the capillary inlet 22 to the capillary outlet 24 (i.e., positive polarity being at the capillary inlet and negative polarity being at the capillary outlet). In 48, the target-binder complexes are detected at the capillary outlet 24, which are substantially separated from the non-binder(s).

With respect to selecting the EOF, in the manner outlined in the above embodiments, the non-binder background level is reduced, therefore providing better separation of the at least one target-binder (TB) complex from the at least one non-binder (N).

With respect to selecting the EOF, the selection may be made to satisfy the relation $v_{TB}>0>v_N$ and thereby satisfy $|\mu_N|>|\mu_{EOF}|>|\mu_{TB}|$. This may be achieved by adjusting the pH of the buffer since vectors E and $\mu_{EOF}$ are in the same direction and/or adjusting the ionic strength of the buffer. In other embodiments, the EOF may be selected by decreasing $|\mu_{EOF}|$ by decreasing the zeta potential of a negatively-charged surface of the inner wall of the capillary (e.g. a fused silica capillary) via either coating the surface with a neutral layer or increasing $I_{RB}$. Increasing $I_{RB}$ makes the buffer resemble physiological ionic strength and permits the selection of binders intended for use in vivo.

In embodiments, the EOF is adjusted by increasing or decreasing a pH of at least one running buffer. The pH may be selected such that there is minimal degradation of the target-binder. In some examples, the pH can be about 5 to about 9, about 6 to about 8, or about 6.5 to about 7.5.

The ionic strength of the buffer can be adjusted using salt(s). Any suitable salt for combining with a buffer may be used to adjust $I_{RB}$. Exemplary salts include, but are not limited thereto, alkali and alkaline earth metal salts (e.g. sodium chloride, sodium iodide, sodium bromide, lithium bromide, lithium iodide, potassium phosphate, sodium bicarbonate, calcium chloride, calcium iodide, calcium bromide, calcium phosphate, calcium bicarbonate, magnesium chloride, magnesium iodide, magnesium bromide, magnesium phosphate, magnesium bicarbonate and the like). In another embodiment, increasing $I_{RB}$ is achieved by increasing the salt concentration of the buffer. Any salt concentration may be used to achieve the desired EOF. In some embodiments, the salt concentration varies from about 0 to about 200 mM in the running buffer. Therefore, wherein $|\mu_N|>|\mu_{EOF}|>|\mu_{TB}|$ may be satisfied by increasing an ionic strength of the at least one running buffer.

In embodiments, $v_{TB}>0>v_N$ was satisfied when $v_N$ was about −1.4 mm/min and $v_{TB}$ was about +15 mm/min. Atypical range of $v_{EOF}$ is from about 15.5 mm/min to about 31.4 mm/min. In other embodiments, the EOF is adjusted so that the equation:

$$(k_N/k_B) \geq 100(N/B)_0 \qquad \text{eq. 3}$$

is satisfied, where $k_N$ is the transmittance for the at least one non-binder, $k_B$ is the transmittance for the at least one binder, and N/B is the non-binder-to-binder ratio. In other embodiments, $k_N$ is less than $1 \times 10^{-6}$. In other embodiments, $k_N$ is from about $6 \times 10^{-10}$ to about $8 \times 10^{-6}$. In still other embodiments, $k_N$ is less than about $6 \times 10^{-10}$. In other embodiments, wherein $k_B$ is about 1.

In other embodiments, wherein the selected EOF is achieved by adjusting pH and/or ionic strength of the at least one running buffer, wherein the pH and/or $I_{RB}$ are selected to such that $v_{TB} = -v_N$ ($v_{TB}$ co-directed with E). The magnitude of the EOF mobility vector, $M_{EOF}$, that corresponds to $v_{TB} = -v_N$ is:

$$M_{EOF} = -\tfrac{1}{2}(\mu_N + \mu_{TB}) \qquad \text{eq. 4}$$

The equation for the vectors is identical to the above for scalar values due to both $\mu_N$ and $\mu_{TB}$ being directed against electric field vector E:

$$M_{EOF} = -\tfrac{1}{2}(\mu_N + \mu_{TB}) \qquad \text{eq. 6}$$

This equality leads to $v_{TB} = -v_N$:

$$v_{TB} = E(\mu_{TB} + M_{EOF}) = E(\mu_{TB} - \tfrac{1}{2}(\mu_N + \mu_{TB})) = \tfrac{1}{2}E(\mu_{TB} - \mu_N)$$

$$v_N = E(\mu_N + M_{EOF}) = E(\mu_N - \tfrac{1}{2}(\mu_N + \mu_{TB})) = \tfrac{1}{2}E(\mu_N - \mu_{TB}) = -v_{TB}$$

Using equation (1) requires knowledge of $\mu_N$ and $\mu_{TB}$. $\mu_N$ is known: $\mu_N = \mu_{DNA} \approx$ about 19 to about 27 mm$^2$/(kVs)$\approx$const (Bao, J. et al. *Anal. Chem.* 2016, 88, 5498-5506). Although, $\mu_N$ may be easily measured if the library is very different from the ones used in Bao. For example, selecting binders from oligonucleotide tagged libraries of molecules, in which the oligonucleotide is double-strand helix, for protein targets, $\mu_{TB}$ may be calculated from:

$$\mu_{TB} = F(\mu_N, d_T, L_{NA}) = \frac{d_T^2 \mu_{TT} + (d_{dsDNA} L_{dsDNA} + d_{ssDNA} L_{ssDNA}) \mu_N}{d_T^2 + d_{dsDNA} L_{dsDNA} + d_{ssDNA} L_{ssDNA}} \qquad \text{eq. 5}$$

Using equation 2 requires knowing $d_T$, $\mu_T$, $\mu_N$, $L_{dsDNA}$, and $L_{ssDNA}$, which can be found as outlined below:

1) $d_T$, the diameter of the target protein, may be found from structural data or accurately estimated from a known diffusion coefficient of the protein, $D_P$, using the Stokes-Einstein equation (M. E. Young, P. A. Carroad and R. L. Bell, *Biotechnol. Bioeng.* 2004, 22, 947-955), $d_T = RT/(3\pi\eta D_T N_A) \; 10^9$ [nm], were R$\approx$8.31 kg m$^2$s$^{-2}$ K$^{-1}$ mol$^{-1}$ is the gas constant, T is the absolute temperature in K, $\eta$ is the solvent viscosity, $D_T$ is the protein's diffusion coefficient, and $N_A \approx 6.02 \times 10^{23}$ mol$^{-1}$ is the Avogadro number;

2) $\mu_T$, the electrophoretic mobility of the target protein, may be determined experimentally by running a pure target protein in CE along with an EOF marker (neutral molecule): $\mu_T = (v_T - v_{EOF})/E$. Here $v_T$ and $v_{EOF}$ may be found by dividing the capillary length, which is from a point where the sample was located at the start time of electrophoresis to a detection point, $l_{cap}$, over the migration times of peaks of the target, $t_T$, and the EOF marker, $t_{EOF}$ (these times are determined directly from the electropherogram): $v_T = l_{cap}/t_T$ and $v_{EOF} = l_{cap}/t_{EOF}$;

3) $\mu_N$ is known as described above;

4) for the DNA moiety, the diameters are $d_{dsDNA} = 2.6$ nm and $d_{ssDNA} = 1.6$ nm, which include the hydration shells around the double-stranded-oligo and single-stranded-oligo regions (B. Schneider, K. Patel and H. M. Berman, *Biophys. J.* 1998, 75, 2422-2434);

5) for the DNA moiety, the lengths of moieties are calculated by $L_{dsDNA} = b_{dsDNA} \times n_{dsDNA}$, $L_{ssDNA} = b_{ssDNA} \times n_{ssDNA}$, where $b_{dsDNA} = 0.34$ nm and $b_{ssDNA} = 0.43$ nm are the lengths of dsDNA and ssDNA monomers and $n_{dsDNA}$ and $n_{ssDNA}$ are numbers of nucleotides in all double-stranded regions and all single-stranded regions, respectively (J. Meagher Robert, J. I. Won, C. McCormick Laurette, S. Nedelcu, M. Bertrand Martin, L. Bertram Jordan, G. Drouin, E. Barron Annelise and W. Slater Gary, *Electrophoresis* 2005, 26, 331-350).

Figure 11A:
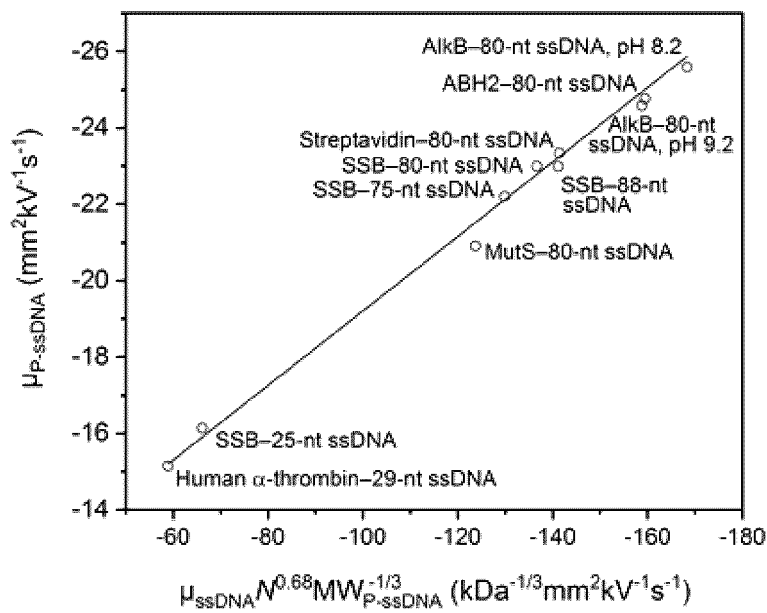
FIGS. 11A and 11B show the dependence of the target-binder (TB) complex mobility for protein targets and ssDNA binders as a linear function of experimentally determined parameters and empirical constants.
Figure 11B:
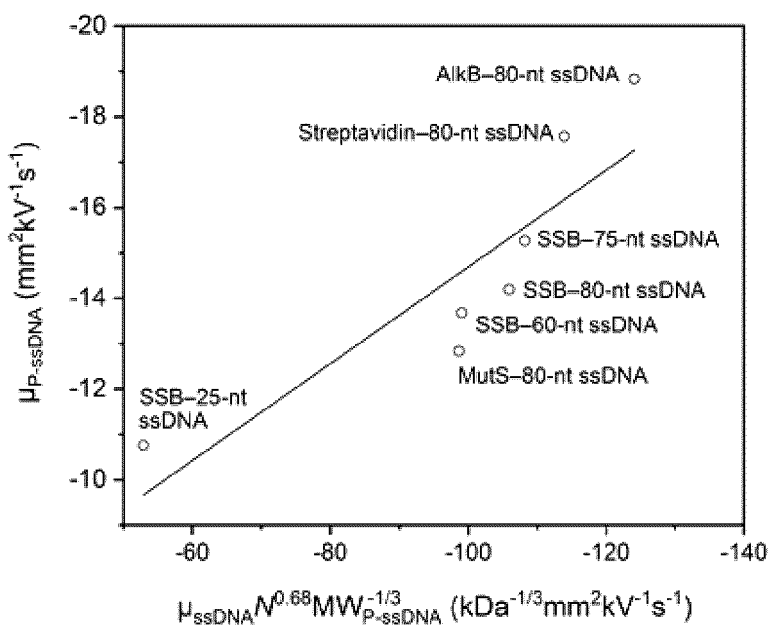

In certain embodiments for selecting binders from random-sequence oligonucleotide libraries, in which the oligonucleotide is single-stranded, for protein targets, $\mu_{TB}$ may be calculated from an empirical model:

$$\mu_{TB} = A + B(\mu_N n_{ssDNA}^{0.68} MW_{TB}^{-1/3}) \qquad \text{eq. 7}$$

where $MW_{TB}$ is the molecular weight of the target-binder complex, A and B are empirical coefficients found by fitting the above function in the experimental data for different TB. In one embodiment, the values of the empirical constants were determined to be: A=−9.95 and B=0.0929. This determination was done for 50 mM Tris-HCl buffer pH 8-9.2 and a set of protein-ssDNA complexes (see FIG. 11A). In another embodiment, the values of the empirical constants were determined to be: A=−10.09 and B=0.2348. This determination was done for 50 mM Tris-HCl buffer pH 7.0 supplemented with 100 nM HCl buffer and a set of protein-ssDNA complexes (see FIG. 11B).

$M_{EOF}$ is calculated, which is used for $v_{TB} = -v_N$, the pH and/or $I_{RB}$ of the running buffer can be determined to provide the desired $M_{EOF}$. This determination can be done, for example, by one of the two approaches:

1) an iterative approach in which $\mu_{EOF}$ is measured for a fixed pair of pH and $I_{RB}$ as a starting point. Further, if $\mu_{EOF} > M_{EOF}$ then $\mu_{EOF}$ is decreased by decreasing pH and/or increasing $I_{RB}$; if $\mu_{EOF} < M_{EOF}$ then $\mu_{EOF}$ is increased by increasing pH and/or decreasing $I_{RB}$. The starting pH and $I_{RB}$ can be similar to physiological ones, pH 7.4 and $I_{RB} = 160$ mM, or any other values.

2) a "rigorous approach" in which a priori determination of an empirical function $\mu_{EOF} = F(pH, I_{RB})$ for a wide range of pH and $I_{RB}$ is performed, and this function is then used to find pH and $I_{RB}$ that allow for $\mu_{EOF} = M_{EOF}$.

Figure 12A:
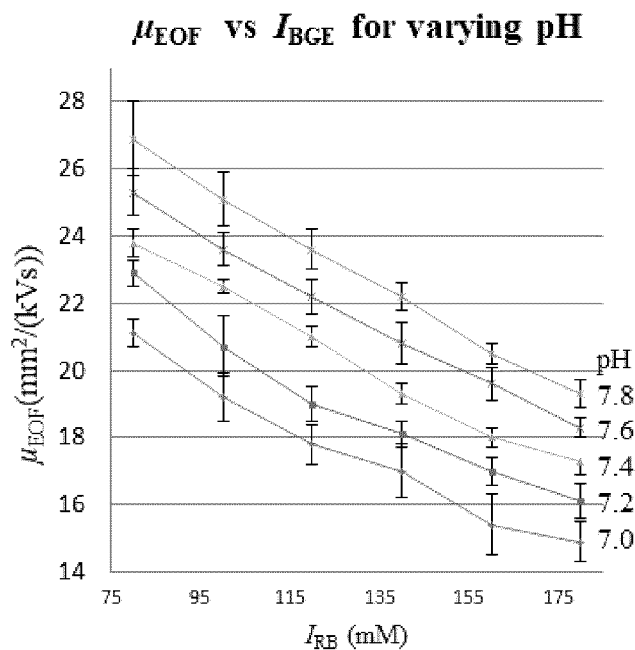
FIGS. 12A and 12B show the effect of pH and ionic strength ($I_{RB}$) of the running buffer on the EOF mobility, $\mu_{EOF}$, for a 50 mM Tris-HCl running buffer supplemented with varying concentrations of NaCl to adjust $I_{RB}$. The two graphs show that $\mu_{EOF}$ can depend linearly on $I_{RB}$ and $1/\mu_{EOF}$ can depend linearly on 1/pH.
Figure 12B:
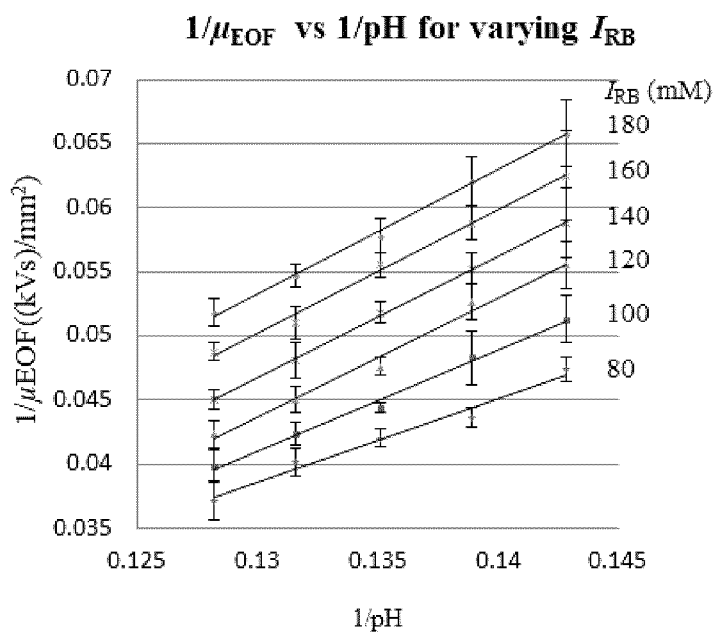

In certain embodiments, the empirical function $\mu_{EOF} = F(pH, I_{RB})$ was determined for one example of the running buffer: 50 mM tris-HCl supplemented with varying concentrations of HCl to adjust $I_{RB}$. The value of $\mu_{EOF}$ was measured for about 7.0 to about 7.8 range of pH values and about 80 to about 180 mM range of $I_{RB}$ values. The results of these measurements are depicted in FIGS. 12A and 12B. The following empirical equation was obtained from the experimental data in FIGS. 12A and 12B:

$$\mu_{EOF} = \left[\left(-0.319 + \frac{4.00}{pH}\right)\left(0.0425 + 0.0164\sqrt{I_{RB}}\right)\right]^{-1} \qquad \text{eq. 8}$$

Multiple pairs of pH and $I_{RB}$ values may satisfy any $\mu_{EOF}$ in the studied range of $\mu_{EOF}$ values, which provides flexibility in choosing pH and $I_{RB}$ of the running buffer depending on a kind of a target used. For example, if a target protein does not tolerate low pH then the desired $\mu_{EOF}$ can be achieved by increasing $I_{RB}$ instead of decreasing pH. The numerical values in eq. 8 can be different for running buffers built upon different types of ions and for different types of capillaries.

With respect to the introduction of the sample into the capillary, the length of the plug introduced may be any suitable length and may vary, for example, from a short (e.g. less than about 1 cm) to greater than about 5 cm and up to about 10 cm. If the sample is introduced electrokinetically, this introduction can be as long as gradual buffer depletion would allow. If a shorter separation time is required, e.g. to reduce the dissociation of target-binder complexes without changing the electric field strength, then a shorter capillary can be used and/or the introduced sample can be propagated from the capillary inlet by pressure difference before an electric field is applied. This propagation can also be done to pass the a region at the capillary inlet where the temperature is not controlled. The propagation may be done to reduce the separation time without having to change the capillary length or an electric field.

In embodiments, the migration of the sample in the capillary is initiated by application of a voltage that is applied between the capillary inlet 22 and capillary outlet 24 and is supplied to the electrodes within the inlet and outlet reservoirs 33, 34 by the high-voltage power supply 25. The resulting electric field is typically from about 50 to about 600 V/cm and more typically from about 100 and about 200 V/cm. Power supplies used in CE typically have reversible polarity, allowing the same instrument to be used in "normal" mode (with detection near the cathode 28 of the capillary) and "reverse" mode (with detection near the anode 26 of the capillary). In the most common mode of CE, all larger ions (e.g. oligonucleotides), positive or negative, are pulled through the capillary in the same direction by the EOF. Separation occurs with migration due to electrophoretic mobility. Typical time windows for target-binder collection are from about 10 min to about 50 min.

Detection by a detector 36 occurs near the outlet end of the capillary. Typical detectors that are used in CE may be, but are not limited to, a mass spectrometer, a light-absorption detection, or a fluorescence detector. The output of the detector 36 is sent for analysis 38 by a device such as an integrator or computer. The data is then displayed as an electropherogram, which reports detector response as a function of time. Separated chemical compounds typically appear as peaks with different migration times in an electropherogram.

In embodiments, the sample may be prepared by any suitable method, for example, an oligonucleotide library of compounds/molecules is combined with at least one target and suitable conditions applied such that the at least one target interacts with at least one of the compounds/molecules of the oligonucleotide library (e.g., binding of the target, catalytically changing the target, reacting with the target in a way that modifies or alters the target or the functional activity of the target, covalently attaching to the target (as in a suicide inhibitor), or non-covalently attaching to the target) to provide at least one target-binder (TB) complex and at least one non-binder (N) (e.g. at least one of the compounds/molecules of the oligonucleotide library that does not bind with the target). In an example, the oligonucleotide library of compounds/molecules is combined with at least one target and incubated at a suitable time and temperature to form at least one target-binder (TB) complex. Such a combination may also be referred to as an equilibrium mixture (i.e. a mixture in which the reaction of binding reached its chemical equilibrium).

With respect to the capillary used in CE herein, any capillary useful for CE may be used. Typically, uncoated fused-silica capillaries are used. In embodiments, the inner diameter ranges from about 25 µm to 100 µm, 50 µm to 100 µm, or 60 µm to 80 µm, more typically, about 75 µm. In embodiments, the outer diameter ranges from about 200 µm to 400 µm, 250 µm to 400 µm, or 300 µm to 400 µm, more typically, about 350 µm. In embodiments, the length of the capillary ranges from about 20 cm to 100 cm, 30 cm to 80 cm, or 40 cm to 60 cm, more typically, about 50 cm. However, other capillary dimensions can be used.

With respect to the capillary used in CE herein, in certain embodiments the capillary is pre-conditioned such that a stable EOF is achieved (e.g. constant $\mu_{EOF}$ in consecutive CE runs). In a specific embodiment, the stability of EOF is achieved by subjecting a new capillary to treatment comprising consecutive rinsing. In one embodiment, a new capillary was used and treated comprising rinsing the capillary with i) at least one alcohol, ii) at least one acid, iii) at least one base, iv) at least one water, and then v) at least one running buffer, and repeating steps ii) to iv) at least once. In another embodiment, a voltage is applied with the running buffer. In a specific embodiment, a capillary was treated comprising: rinsing with MeOH for 10 min at 20 psi; rinsing with 100 mM HCl for 3 min at 20 psi; rinsing with 100 mM NaOH for 6 min at 20 psi; rinsing with distilled water for 3 min at 20 psi; rinsing with the running buffer for 40 min at 40 psi; rinsing with 100 mM HCl for 3 min at 20 psi; rinsing with 100 mM NaOH for 3 min at 20 psi; rinsing with the running buffer for 3 min at 20 psi; rinsing with the running buffer for 3 min at 20 psi; applying voltage with the running buffer for 30 min and 10 kV. During the first five rinses the temperature of the capillary is about 25° C. and the second five rinses, the temperature is about 15° C.

The above disclosure generally describes the present invention. A more complete understanding can be obtained by reference to the following specific examples. These examples are provided for purposes of illustration only, and are not intended to be limiting unless otherwise specified. Thus, the invention should in no way be construed as being limited to the following examples, but rather, should be construed to encompass any and all variations which become evident as a result of the teaching provided herein.

Without further description, it is believed that one of ordinary skill in the art can, using the preceding description and the following illustrative examples, make and utilize the methods of the present invention and practice the claimed methods. The following working examples therefore, specifically point out the typical aspects of the present invention, and are not to be construed as limiting in any way the remainder of the disclosure.

EXAMPLES

Example 1

Materials, Procedures, and Equipment Used in Example 1

All chemicals utilized were manufactured by Sigma-Aldrich (Oakville, ON, Canada) unless otherwise stated. Fused-silica capillaries with inner and outer diameters of 75 and 360 µm, respectively, were manufactured by Molex Polymicro (Phoenix, AZ, USA). Recombinant Thermus aquaticus MutS protein (MW≈90 kDa, pI 6.0) was expressed and purified as described previously. All DNA molecules were custom synthesized by Integrated DNA Technologies (Coralville, IA, USA). Bodipy (4,4-difluoro-4-bora-3a,4a-diaza-s-indacene) was produced by Life Technologies Inc.

(Burlington, ON, Canada). The CE buffer) was 50 mM Tris-HCl with NaCl ranging from 0 to 150 mM at pH 7.0. The sample buffer was the same as the buffer to prevent advert effects of buffer mismatch. Accordingly, all dilutions of sample components used in CE experiments were done by adding the corresponding buffer.

DNA Sequences

The DNA aptamer with affinity toward MutS protein was previously selected in our laboratory (clone 2-06), (Drabovich, A. P.; Berezovski, M.; Okhonin, V.; Krylov, S. N. *Anal. Chem.* 2006, 78, 3171-3178) and its fluorescein amidite (FAM)-labeled version was used here: 5'-FAM-CTT CTG CCC GCC TOO TTC CTG GTA AAG TO A TTA ATA GGT GTG GGG TGC CGG GCA TTT CGG AGA CGA GAT AGG CGG ACA CT-3'. For aptamer-selection study, a synthetic FAM-labeled DNA library (N40) with a 40-nt random region was used: 5'-FAM-AGC CTA ACG CAG AAC AAT GG-(N40)-CGA TGC CAG GTT AAA GCA CT-3'. The following primers were used for PCR amplification of the MutS aptamer: forward primer (MutS_uF), 5'-CTT CTG CCC GCC TCC TTC C-3'; reverse primer (MutS_uR), 5'-AGT GTC CGC CTA TCT CGT CTC C-3'. Two sets of primers were used to amplify binders selected from the naïve library. The first set of primers was an unlabeled forward primer (N40_uF), 5'-AGC CTA ACG CAG AAC AAT GG-3', and an unlabeled reverse primer (N40_uR), 5'-AGT GCT TTA ACC TGG CAT CG-3'. The second set contained a FAM-labeled forward primer (N40-famF), 5'-FAM-AGC CTA ACG CAG AAC AAT GG-3', and a biotin-labeled reverse primer (N40-biotinR), 5'-Biotin-TEG-AGT GCT TTA ACC TGG CAT CG-3'.

Default Conditions for CE and Fraction Collection

All CE experiments were performed with a P/ACE MDQ™ apparatus (SCIEX, Concord, ON, Canada) equipped with a laser-induced fluorescence (LIF) detection system. Fluorescence was excited with a blue line (488 nm) of a solid-state laser and detected at 520 nm using a spectrally-optimized emission filter system. Uncoated fused-silica capillaries, with a total length of 50 cm and a 10.2 cm distance from one of the ends to the detection zone were used. The two capillary ends were used as inlets interchangeably in experiments requiring different separation distances. Prior to every run, the capillary was rinsed successively with 0.1 M HCl, 0.1 M NaOH, deionized $H_2O$, and a run buffer for 3 min each. The sample contained 10 µM annealed oligonucleotides (melted at 90° C. for 2 min and gradually cooled down to 20° C. at a rate of 0.5° C./min) and 150 nM Bodipy. When specified, the sample also contained 100 nM MutS protein. The sample mixture was incubated for 30 min at a room temperature (22-24° C.) and then injected with a pressure pulse of 0.5 psi×10 s to yield a 10 mm long sample plug. The injected sample plug was propagated through the uncooled part of the capillary at the inlet by injecting a 5.7 cm long plug of the buffer with a pressure pulse of 0.3 psi×90 s. For fraction collection experiment, CE was carried out at an electric field of 200 V/cm (10 kV over 50 cm) for 64 min. Collection vials contained 20 µL of the buffer each and were switched every 2 min; 32 fractions were collected.

Quantitative PCR

DNA in the collected fractions was amplified and quantitated by qPCR using a CFX Connect™ instrument from Bio-rad. q-PCR reagent mixture was prepared by combining IQ SYBR Green Supermix from Bio-Rad (Mississauga, ON, Canada) with unlabeled DNA primers at final concentrations of 1×SYBR Green Supermix, 100 nM MutS_uF, and 100 nM MutS_uR. qPCR reaction mixture was prepared by adding 18 µL of the qPCR reagent mixture to a 2-µL aliquot of each fraction immediately before thermocycling. The thermocycling protocol was: 95° C. for 3 min, 95° C. for 10 s (denaturation), 56° C. for 10 s (annealing), 72° C. for 10 s (extension), followed by a plate read at 72° C. and a return to the denaturation step (bypassing the 95° C.×3 min step) for a total of 43 cycles. All reactions were performed in duplicates.

Experiment 1

The sample was an equilibrium mixture of MutS protein with its fluorescently-labeled DNA aptamer. The equilibrium mixture contained the protein-aptamer (target-binder) complex and an unbound aptamer (non-binder). The equilibrium mixture in this example contained 100 nM MutS, 100 nM fluorescently-labeled aptamer, and 150 nM Bodipy (uncharged fluorophore, EOF marker) and was incubated for 30 min at room temperature. To achieve fast separation, a very short (4.5 cm) separation distance, defined as the distance in the capillary from the point of electric field application to the detection point, was used. CE was carried out at E=200 V/cm with on-line fluorescence detection. No peaks were observed after 30 min; therefore, only the first 30 min of 50-min runs are shown in both panels. FIG. 5 shows the equilibrium mixtures run with a positive polarity at the capillary inlet 22. FIG. 5B shows the equilibrium mixtures run with a negative polarity at the capillary inlet to detect non-binders when $v_N<0$.

Figure 6A:
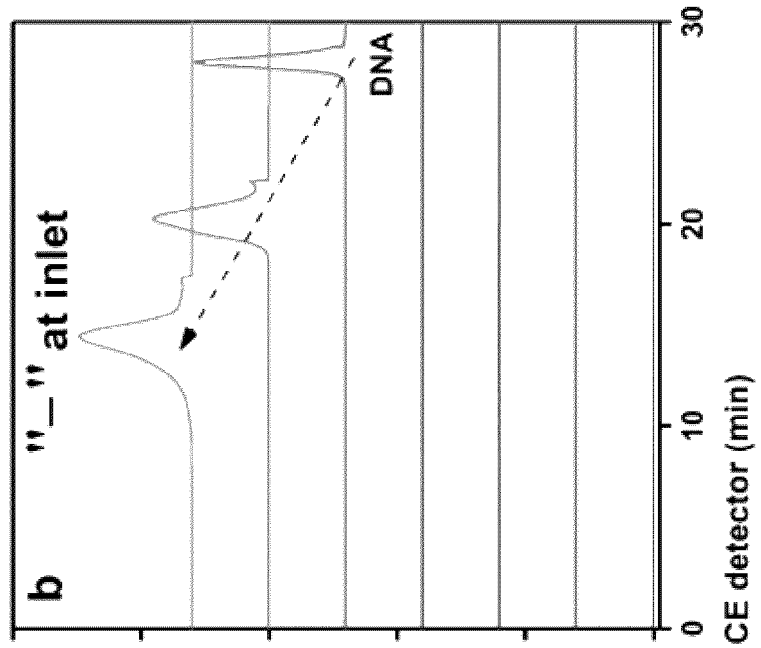
FIG. 6A shows a graph depicting examples of times for the detection of target-binder complexes to reach the detector when utilizing the method of FIG. 5 with the anode at the inlet.

FIG. 6A shows that the peak of the target-binder complex was detected only with positive charge at the inlet and for all concentrations of NaCl suggesting that $v_{TB}>0$ for all $I_{RB}$ values studied. The peak of non-binders was detected with positive polarity at the capillary inlet 22 for [NaCl]≤50 mM, and with negative polarity at the inlet for [NaCl]≥100 mM, suggesting that $v_N>0.9$ mm/min (4.5 cm/50 min) for [NaCl] <50 mM and $v_N<-0.9$ mm/min for [NaCl]≥100 mM. The peak of non-binders was not detected with either polarity within 50-min runs for [NaCl]=75 mM suggesting that this concentration corresponded to $|v_N|<0.9$ mm/min. Therefore, by increasing the $I_{RB}$ while keeping complex migration to the capillary output under 1 h, $v_{TB}>0>v_N$ was satisfied. In this example, when the concentration of NaCl in buffer was equal to or greater than 100 mM, the condition of $v_{TB}>0>v_N$ was also satisfied.

Figure 6B:
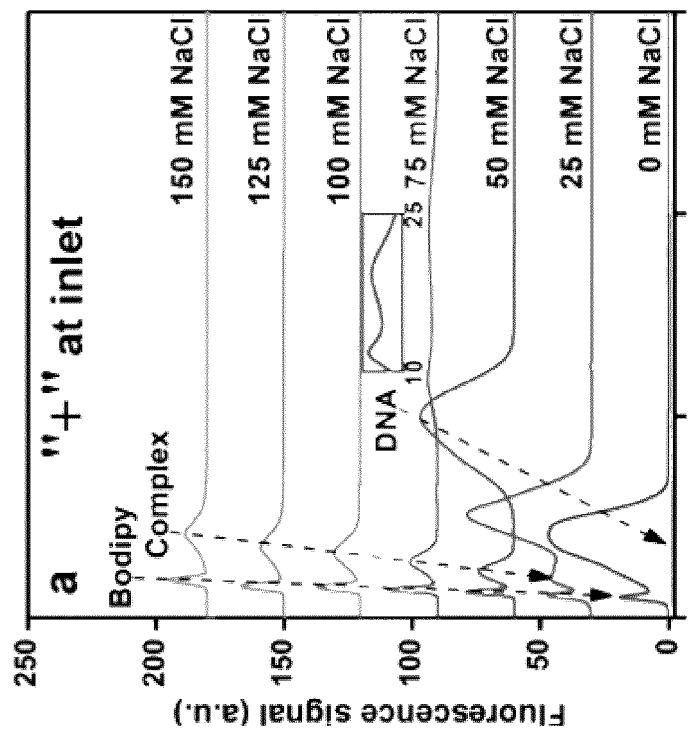
FIG. 6B shows a graph depicting examples of times for the detection of non-binder to reach the detector when utilizing the method of FIG. 5 with the exception of the cathode being at the inlet.

FIG. 6B shows that the peak of the non-binder was detected only with negative charge at the inlet and for [NaCl]≥100 mM.

Experiment 2

Figure 6C:
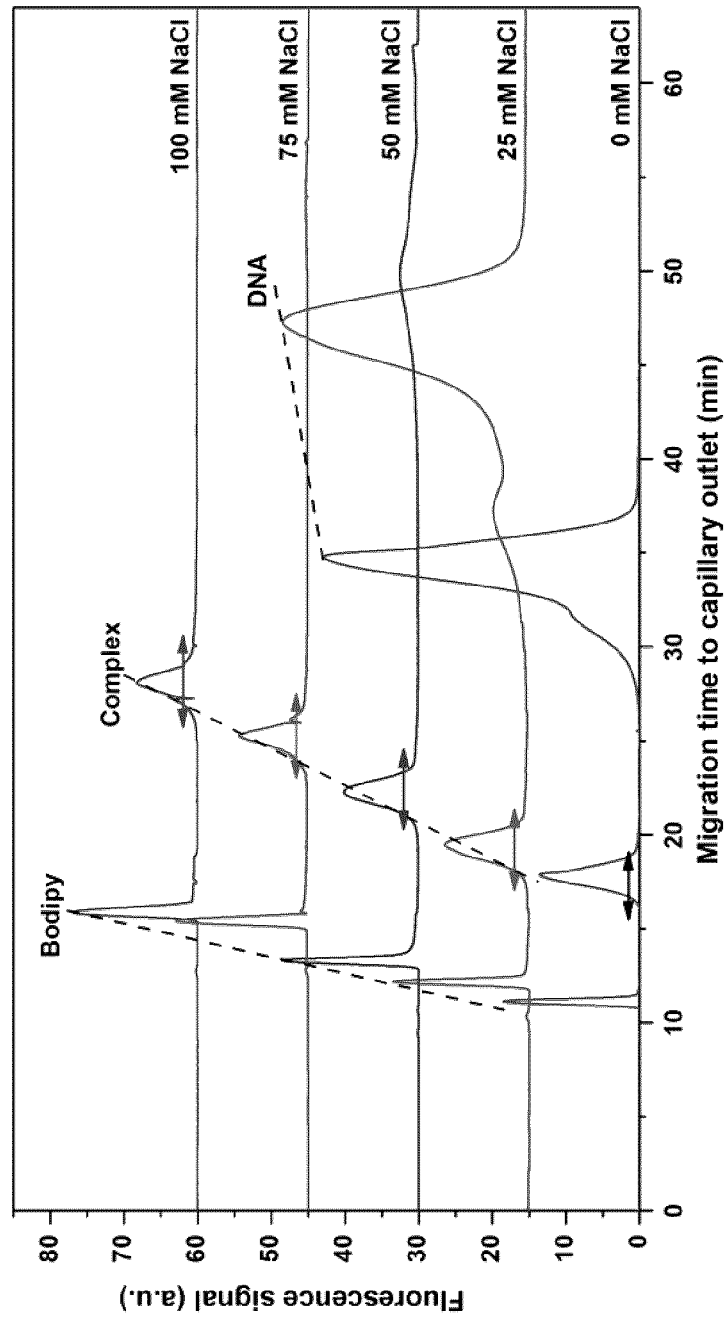
FIG. 6C shows another example of migration times of target-binder complexes to the capillary outlet utilizing the method of FIG. 5B.

FIG. 6C shows another example, in which $I_{RB}$ (represented by concentration of added NaCl) was studied with regards to its effect on non-binder background quantitatively expressed by the value of $k_N$. For different concentrations of NaCl in RB, the following values of $k_N$ were obtained about $8\times10^{-6}$ (0 mM NaCl), about $6\times10^{-7}$ (25 mM NaCl), about $2\times10^{-8}$ (50 mM NaCl), about $9\times10^{-9}$ (75 mM NaCl), and about $<6\times10^{-10}$ (100 mM NaCl). These CE experiments were conducted with a 34-cm separation distance, which can be used in practical CE-based separation for binder selection (Berezovski et al., *Non-SELEX selection of aptamers. J. Am. Chem. Soc.* 2006, 128, 1410-1411). CE was carried out with an electric field of 200 V/cm, positive polarity at the capillary inlet 22, and a separation distance of 34 cm. The sample was the DNA aptamer (that binds to MutS); this aptamer may then be considered the non-binder. Two-minute fractions were collected and DNA aptamer amounts in them were determined via qPCR. FIG. 6C shows the determination of time windows for MutS-aptamer complex collection for buffers based on 50 mM Tris-HCl pH 7.0 and containing concentrations of NaCl varying from 0 to 100 mM. The equilibrium mixture contained 100 nM MutS, 100 nM fluorescently-labeled aptamer, and 150 nM Bodipy (EOF marker). The double-headed arrows indicate estimated elution windows of the MutS-aptamer complex.

Figure 7:
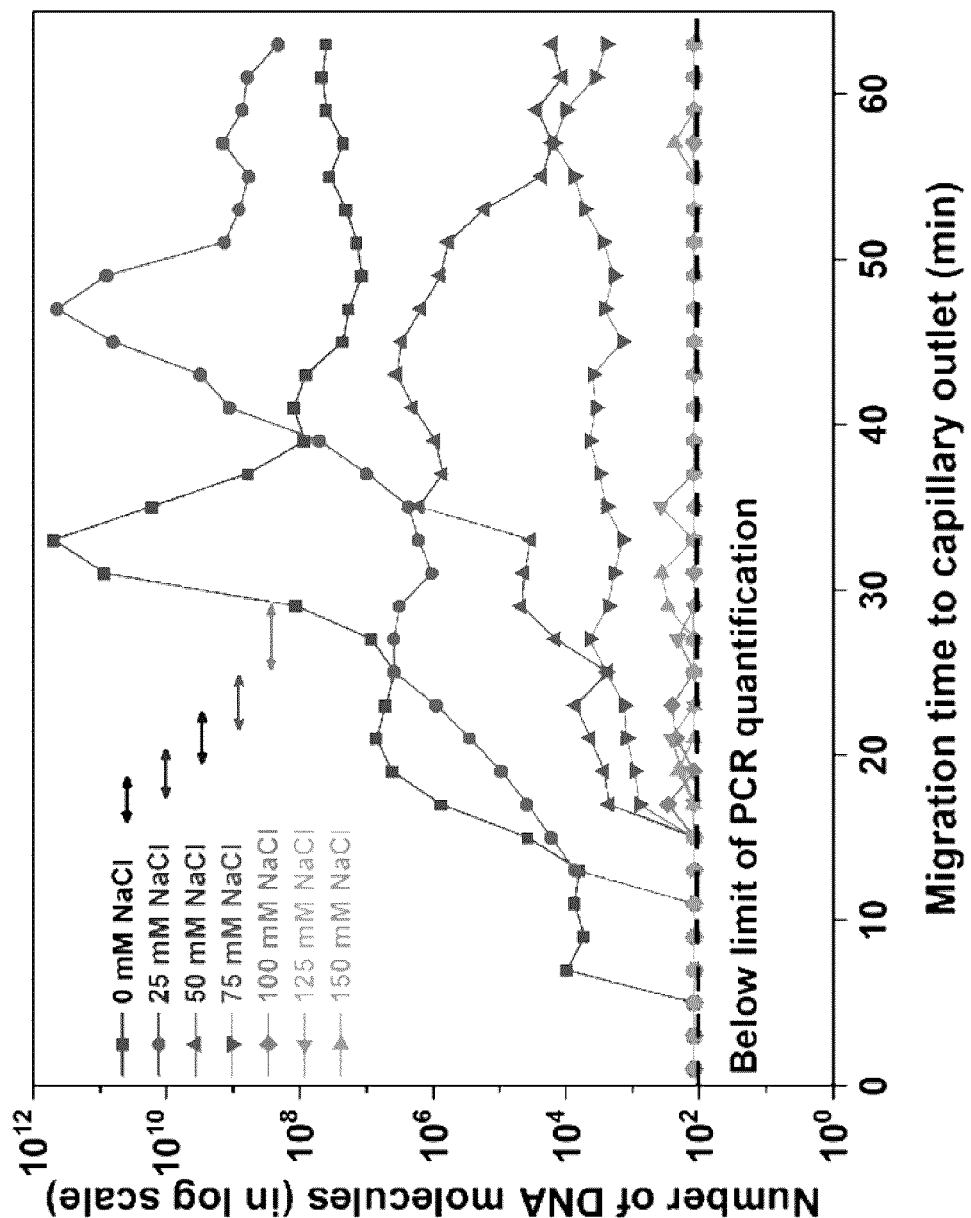
FIG. 7 shows the results for the example of FIG. 6C presented as electropherograms with a log number of DNA molecules in a corresponding fraction (collected at the capillary outlet) on the y axis.

FIG. 7 shows the results for an example similar to that shown in FIG. 6C but in the presence of MutS to determine binder-collection time windows required for accurate assessment of $k_N$. The non-binder background decreased to and below the limit of quantitation (LOQ) of qPCR at [NaCl] ≥100 mM. Calculating $k_N$ entails specifying a specific binder-collection time window. Time windows used in this example corresponded to elution of MutS-aptamer complexes. Such time windows were determined in a separate set of CE experiments with fluorescence detection utilizing the MutS-aptamer (target-binder) equilibrium mixture in which the aptamer was fluorescently labeled (FIG. 6C). These time windows were defined as widths of the bases of peaks of target-binder complexes in FIG. 6C and are shown in FIG. 7 as horizontal double-headed arrows. The values of k were calculated as integrals under DNA curves within the corresponding time windows divided by the total amount of DNA sampled (e.g. the total amount mimics the amount of the sampled library that is typically dominated by the non-binders (e.g. $10^5$ non-binders per 1 binder) into the capillary 20. The total amount of injected DNA samples was calculated as an integral under the DNA curve for [NaCl]=0 within a time window 0-50 min. For different concentrations of NaCl in buffer we obtained the following values of $k_N$: $8\times10^{-6}$ (0 mM NaCl), $6\times10^{-7}$ (25 mM NaCl), $2\times10^{-8}$ (50 mM NaCl), $9\times10^{-9}$ (75 mM NaCl), and $<6\times10^{-10}$ (100 mM NaCl). Adding 100 mM NaCl to buffer, i.e., satisfying conditions of $v_N<0<v_{TB}$, resulted in >$1.3\times10^4$ times decrease in $k_N$ in comparison to no NaCl in buffer. The value of $k_N$ for 100 mM NaCl is not exact but rather an upper limit due to the assumption that the amount of DNA samples was equal to the LOQ of qPCR if it was below LOQ.

These examples showed that $v_{TB}>0>v_N$ could decrease the non-binder background and achieve $k_N<6\times10^{-10}$. This value is over 10,000 times lower than the lowest previously reported $k_N$ of $10^{-5}$ in other methods (Berezovski et al., *Nonequilibrium capillary electrophoresis of equilibrium mixtures; a universal tool for development of aptamers. J. Am. Chem. Soc.* 2005, 127, 3165-3171; Drabovich et al., *Selection of smart aptamers by methods of kinetic capillary electrophoresis. Anal. Chem.* 2006, 78, 3171-3178).

In the above examples, it was assumed that $k_B \approx 1$, and $k_B/k_N$ was anticipated to be predominantly defined by $k_N$. In partitioning above, $k_B$ is equal to unity for a target that does not adsorb onto the inner capillary wall unless the binder-collection time window is chosen incorrectly. To validate the above, $k_B$ was found experimentally as $k_B = B_{out}/B_{in}$, where $B_{in}$ is the number of target-binder complexes sampled and $B_{out}$ is the number of binders collected in the binder collection time window corresponding to the elution time window of the target-binder complexes. NaCl-free buffer, in which the target-binder complexes and non-binders migrate in the same direction (FIG. 2B), allowed for accurate determination of $B_{in}$ by using fluorescence detection (FIG. 8A) (Berezovski et al., *Nonequilibrium capillary electrophoresis of equilibrium mixtures; a universal tool for development of aptamers. J. Am. Chem. Soc.* 2005, 127, 3165-3171; Berezovski et al., *Non-SELEX selection of aptamers. J. Am. Chem. Soc.* 2006, 128, 1410-1411). A known volume of the equilibrium mixture containing MutS and its DNA aptamer (binder) was sampled for a CE run, in which both fluorescence and qPCR detections were used leading to two electropherograms for each CE run (FIGS. 8A, 8B).

The value of $B_{in}=(8.9\pm0.9)\times10^8$ was found from an electropherogram with fluorescence detection shown in FIG. 8A as the multiplication product of (i) the total concentration of aptamer in the equilibrium mixture, (ii) the volume of the sampled equilibrium mixture, and (iii) a relative amount of aptamer that was bound to MutS in the equilibrium mixture (relative to the total sampled amount of aptamer). No correction was made for complex dissociation during CE as less than 1% of the MutS-aptamer complex dissociated during complex migration to the capillary outlet 24.

The value of $B_{out}=(9.2\pm0.4)\times10^8$ was then determined from the electropherogram with qPCR detection shown in FIG. 8B by calculating an integral under the DNA curve within the binder-collection time window of 15 to 23 min. $B_{out}$ and $B_{in}$ were calculated to be $k_B \equiv B_{out}/B_{in}=1.0\pm0.1$.

Using $v_{T-B}>0>v_N$, CE was conducted (with buffer containing 100 mM NaCl) and found $B_{out}=(7.3\pm0.5)\times10^8$, which is slightly lower than the value of $(9.2\pm0.4)\times10^8$ obtained for NaCl-free buffer. The difference was presumably due to additional ions' affecting the strength of ionic bonds in protein-DNA (target-binder) complexes. These experiments demonstrated that by choosing a proper binder-collection time window, $k_B \approx 1$.

Experiment 3

Figure 9:
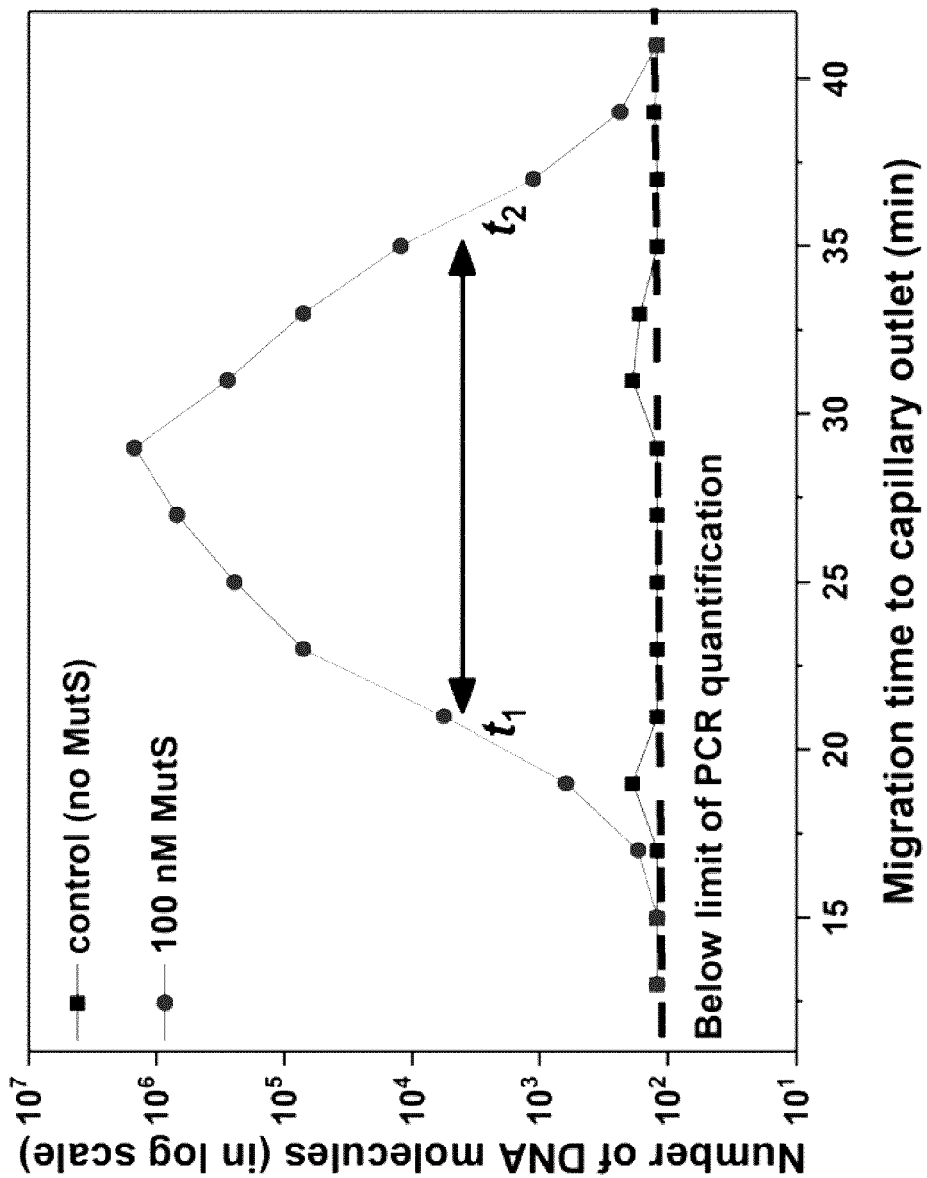
FIG. 9 shows two electropherograms of an example of CE-based selection of aptamers. One electropherogram corresponds to about 100 nM target (MutS protein) in the equilibrium mixture, while the other corresponds to a control in which the target in the equilibrium mixture was replaced with buffer. Two-minute fractions were collected and analyzed by qPCR for both cases.

To test if the achieved value of $k_B/k_N>1.7\times10^9$ (e.g. $1/6\times10^{-10}$) in separation by $v_{TB}>0>v_N$ CE could facilitate one-round selection of aptamers, selection of MutS binders from a naïve DNA library was conducted. Forty-seven nanoliters of the equilibrium mixture of the library ((B+N)$_0=2.8\times10^{11}$) and 100 nM MutS was subjected to $v_{TB}>0>v_N$ CE (with buffer containing 100 mM NaCl). Two-minute fractions were collected and analyzed by qPCR to build an electropherogram; the control experiment was similar, but the target in the equilibrium mixture was replaced by buffer (FIG. 9). The collected fractions were analyzed within the wide binder-collection time window of 13 to 41 min. The numbers of binders and non-binders at the output of selection were calculated as integrals under the corresponding curves within the binder-collection time window in $v_{TB}>0>v_N$-based separation and the control experiment, respectively: $B_{out} \approx 1.0\times10^6$ and $N_{out} \approx 4\times10^2$. FIG. 9 shows a peak of target-binder complexes in $v_{TB}>0>v_N$ CE which is absent in the control experiment. It was calculated that $(B/N)_1=B_{out}/N_{out} \approx (2.9\times10^6)/(1.1\times10^3) \approx 2.6\times10^3$. Thus, $(B/N)_1 >> 100$, which confirms completed selection using the criterion of selection completion defined above: (B/N)$_1 \geq 100$. The knowledge of the amount of the sampled library (B+N)$_0=2.8\times10^{11}$ (which can be assumed to be equal to $N_{in}$) and the amount of binders at the output of separation $B_{out} \approx 2.9\times10^6$ (which can be used to define $B_{in}$) allows estimation of the initial binder abundance, (B/N)$_0 \equiv B_{in}/N_{in}$ to be approximately $2.9\times10^6/2.8\times10^{11} \approx 1.0\times10^{-5}$. In other words, approximately 1 out of every hundred thousand molecules of the naïve DNA library was bound to MutS in the equilibrium mixture containing 100 nM MutS and stayed bound for the duration of the CE run.

Figure 10:
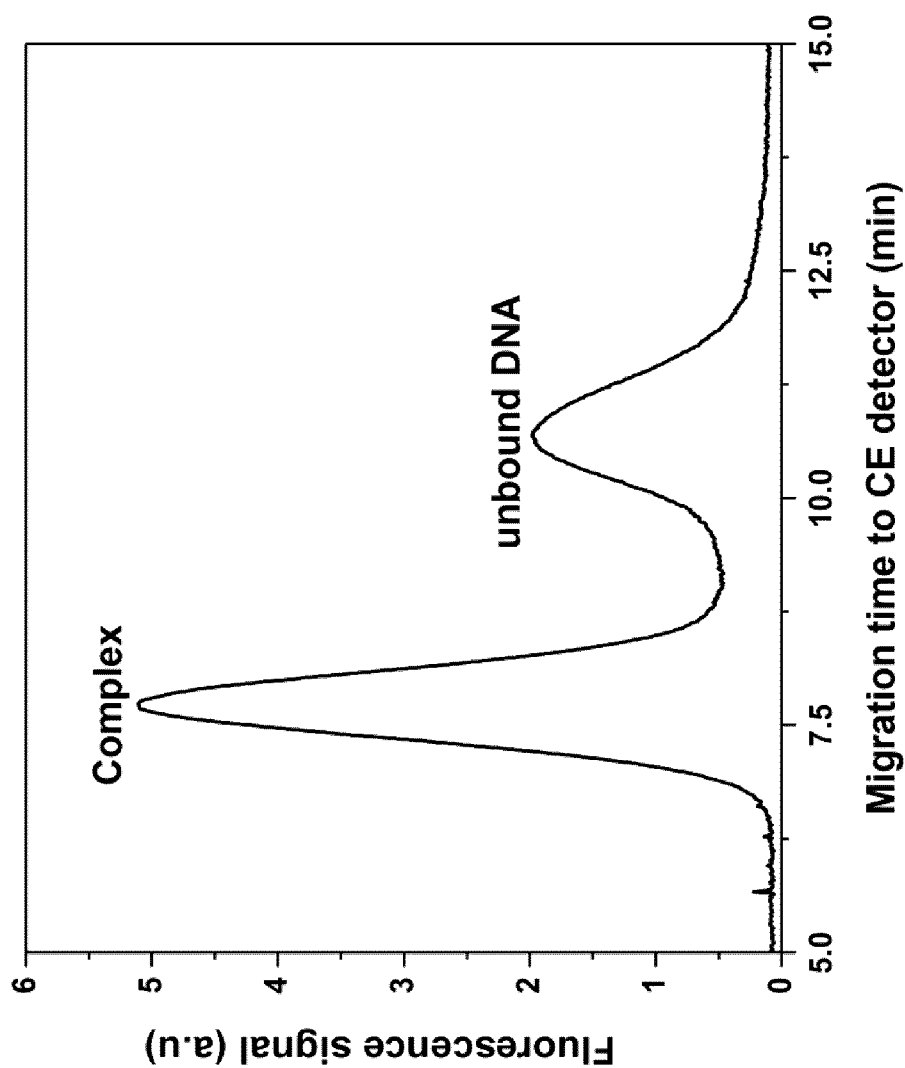
FIG. 10 shows fluorescence detection of MutS-binder complexes and non-binder (e.g. unbound DNA) in an example of pressure-assisted CE performed after amplifying DNA, selected from the example shown in FIG. 9, with preparative PCR.

A fraction containing the highest amount of target-binder complexes (a fraction that eluted at 29 min) was amplified by PCR using a fluorescently-labeled primer. Alternatively, multiple fractions within a 15 to 40 min time window may be combined and amplified to increase the amount of DNA material. After amplifying DNA in this fraction, a classical CE-based binding test was performed with fluorescence detection (see FIG. 10) (Kanoatov et al., Analysis of DNA in Phosphate Buffered Saline Using Kinetic Capillary Electrophoresis. *Anal. Chem.* 2016, 88, 7421-7428). This test revealed an apparent equilibrium dissociation constant of the enriched library of $K_{d,app}$=37 nM and confirmed successful selection of a high-affinity aptamer pool in a single round of $v_{TB}$>0>$v_N$ CE separation. For comparison, selecting a pool with similar $K_{d,app}$ by classical CE-based separation required three rounds of SELEX (Drabovich et al., *Selection of smart aptamers by methods of kinetic capillary electrophoresis. Anal. Chem.* 2006, 78, 3171-3178).

Experiment 4—Single-Round Aptamer Selection for MutS Protein

Fraction collection and qPCR detection were similar to the procedures described in the previous two sections with a few modifications specified below. The equilibrium mixture contained: 10 µM N40 library, 100 nM MutS protein, and 150 nM Bodipy. For qPCR, 1×SYBR Green Supermix and the unlabeled primers for N40 library (100 nM of each N40_uF and N40_uR) constituted the qPCR reagent mixture. The fraction which eluted at minute 29 and contained the highest amount of MutS-DNA complexes was subjected to preparative PCR. The procedure of preparative PCR involved two rounds of amplification. In the first round, the fraction was amplified by qPCR in quintuplicates as previously described. An S-shaped amplification curve was plotted, and the PCR product was removed two cycles into the exponential phase of the curve. After qPCR, 100 µL of the five combined PCR reactions was purified using MinElute® PCR purification kit (QIAGEN, Missisauga, ON, Canada) as per manufacturer's instructions. DNA was then eluted using 20 µL of 50 mM TrisHCl, pH 7.0. Once product's purity was verified by native PAGE, it was subjected to asymmetric PCR. Five µL of DNA was added to 45 µL of asymmetric PCR reagent mixture from New England Biolabs Inc. (MA, USA). Final concentrations of PCR reagents in the reaction mixture were: 1× Standard Taq Reaction Buffer, 1 µM N40-famF, 50 nM N40-biotinR, 2.5 units/µL Taq DNA Polymerase, and 200 µM dNTPs mix. The reaction was performed in duplicates with the following temperature protocol: 94° C. for 30 s (initial denaturation, performed once), 94° C. for 10 s (denaturation), 56° C. for 10 s (annealing), and 72° C. for 10 s (extension). Seventeen cycles of asymmetric PCR were run. Ten µL of Magna-Bind™ streptavidin beads suspension (Thermo Scientific, IL, USA) was washed three times and resuspended in bead washing/binding buffer (10 mM Tris-HCl, 50 mM NaCl, 1 mM EDTA pH 8.0). Once amplified, the duplicate PCR reactions were combined and incubated with streptavidin magnetic beads for 30 min at room temperature. The beads were magnetized, discarded, and the PCR product was then purified using the MinElute® PCR purification kit. The final product was eluted using 20 µL of 50 mM TrisHCl, pH 7.0, and 2 µL of 1 M NaCl was added to bring NaCl concentration to 100 mM.

To determine DNA concentration in the enriched library pool, serial dilutions of N40-famF (2 µM, 1 µM, 500 nM, 250 nM, 125 nM, 62.5 nM, and 31.25 nM) were prepared to build a standard curve by measuring fluorescence intensity at 519 nM with NanoDrop 3300 Fluorospectrometer (Thermo Scientific, IL, USA). DNA concentration in the enriched library pool was found to be 1.2 µM.

For a pressure-aided one-round selection of aptamers-based binding test of the enriched pool (used to determine $K_{d,app}$), a 47 nL plug of the equilibrium mixture containing 20 nM enriched library and 100 nM MutS in 50 mM Tris-HCl, 100 mM NaCl, pH 7.0, (default running buffer for one-round selection of aptamers) was injected into 50-cm-long capillary by a 0.5 psi×10 s pressure pulse. The sample mixture was propagated through the non-cooled portion of the capillary by injecting a 5.7-cm-long plug of buffer with a pressure pulse of 0.3 psi×90 s. CE was carried out at an electric field of 200 V/cm with "+" at the inlet. In addition to applying voltage, a pressure of 0.20 psi was applied to the capillary inlet to supplement the electric field and ensure that the Non-binders reach the detector. The pressure-aided one-round selection of aptamers allowed detection of Target-binder complexes and Non-binders, which is required for determination of $K_{d,app}$.

Example 2: Capillary Pre-Conditioning for Reproducible EOF

The binder-selection method can depend on how close the experimental mobility of EOF, $\mu_{EOF}$, is to the selected (desirable) mobility, $M_{EOF}=-\frac{1}{2}(\mu_N+\mu_{TB})$. The value of $\mu_{EOF}$ can depend on pH and $I_{RB}$ but it can also depend on how the capillary inner surface was treated (pre-conditioned) before binder selection. Typically, a pre-conditioning procedure can provide stable EOF (constant $\mu_{EOF}$) in consecutive CE runs.

Experiment 1

Materials, Procedures, and Equipment Used in Experiment 1

All chemicals utilized were manufactured by Sigma-Aldrich (Oakville, ON, Canada) unless otherwise stated. Fused-silica capillaries with inner and outer diameters of 75 and 360 µm, respectively, were manufactured by Molex Polymicro (Phoenix, AZ, USA). Bodipy (4,4-difluoro-4-bora-3a,4a-diaza-s-indacene) was produced by Life Technologies Inc. (Burlington, ON, Canada). Two sets of CE running buffers were used. The first set of CE running buffers was 50 mM Tris-HCl with NaCl ranging from 0 to 150 mM at pH 7.4. The second set of CE running buffers was Tris-HCl with ionic strength of 191 mM at three different pH values: 7.4, 7.8 and 8.0. The sample buffer was the same as the CE running buffer to prevent advert effects of buffer mismatch. Accordingly, all dilutions of sample components used in CE experiments were done by adding the corresponding CE running buffer.

Default Conditions for Measuring Mobilities of EOF:

All CE experiments were performed with a P/ACE MDQ™ apparatus (SCIEX, Concord, ON, Canada) equipped with a laser-induced fluorescence (LIF) detection system. Fluorescence was excited with a blue line (488 nm) of a solid-state laser and detected at 520 nm using a spectrally-optimized emission filter system. Uncoated fused-silica capillaries, with a total length of 50 cm and a 10.2 cm distance from one of the ends to the detection zone were used. Prior to each set of measurements for one CE buffer, the capillary was preconditioned with the method stated in protocol 3. Between the runs with the same buffer, the capillary was only rinsed by the corresponding CE buffer for 3 min at 20.0 psi. The sample contained 500 nM Bodipy and was injected with a pressure pulse of 0.5 psi×10 s to yield a 10 mm long sample plug. The injected sample plug was propagated through the uncooled part of the capillary at the inlet by injecting a 5.7 cm long plug of the buffer with a pressure pulse of 0.3 psi×90 s. For $\mu_{EOF}$ measuring experiment, CE was carried out at an electric field of 200 V/cm (10 kV over 50 cm) for 20 min.

Pre-Conditioning Protocols

Protocol 1. Standard Pre-Conditioning Procedure

Brand new bare silica capillary with inner diameter of 75 μm and total length of 50 cm was rinsed with methanol for 10 min at 20 psi (50 capillary volumes) and then with each of the following solutions: 0.1 M HCl, 0.1 M NaOH and deionized water for 3 min at 20 psi each (15 capillary volumes per solution). Next, the capillary was rinsed with the running buffer (50 mM Tris-HCl+100 mM NaCl, pH 7.0) for 10 min at 10 psi (25 capillary volumes). Upon completion of the rinsing, an electric field of 200 V/cm was applied to the capillary for 10 min to finish the equilibration. At every step the temperature of the capillary was kept at 15° C.

Protocol 2. Overnight Pre-Conditioning Procedure

Brand new bare silica capillary with inner diameter of 75 μm and total length of 50 cm was pre-conditioned in exactly same way as described in Protocol 1. Then, capillary pre-filled with the running buffer was left overnight (approximately for 10 h) at 25° C.

Protocol 3. Modified Pre-Conditioning Procedure

Step 1. Brand new bare silica capillary with inner diameter of 75 μm and total length of 50 cm was sequentially rinsed with each of the following solutions: methanol for 10 min at 20 psi (50 capillary volumes), 0.1 M HCl for 3 min at 20 psi (15 capillary volumes), 0.1 M NaOH for 6 min at 20 psi (30 capillary volumes), deionized water for 3 min at 20 psi (15 capillary volumes) and running buffer (50 mM Tris-HCl+100 mM NaCl, pH 7.0) for 40 min at 40 psi (410 capillary volumes). At step 1 the temperature of the capillary was kept at 25° C.

Step 2. After completion of step 1, capillary was rinsed with each of the following solutions: 0.1 M HCl, 0.1 M NaOH, deionized water and running buffer for 3 min at 20 psi each (15 capillary volumes per solution). Upon completion of step 2, an electric field of 200 V/cm was applied to the capillary for 30 min to finish the equilibration. At step 2 the temperature of the capillary was kept at 15° C.

Results of Experiment 1

The stability of EOF in a series of consecutive CE runs was studied for varying methods of capillary-surface pre-conditioning. First, a standard short pre-conditioning procedure (Protocol 1) was used followed by a consecutive CE runs of an EOF marker (Bodipy, electrically-neutral molecule). It was found that $\mu_{EOF}$ increased from run to run during 6 consecutive runs until a stable value of EOF was reached (FIG. 33, Line 1).

Figure 13:
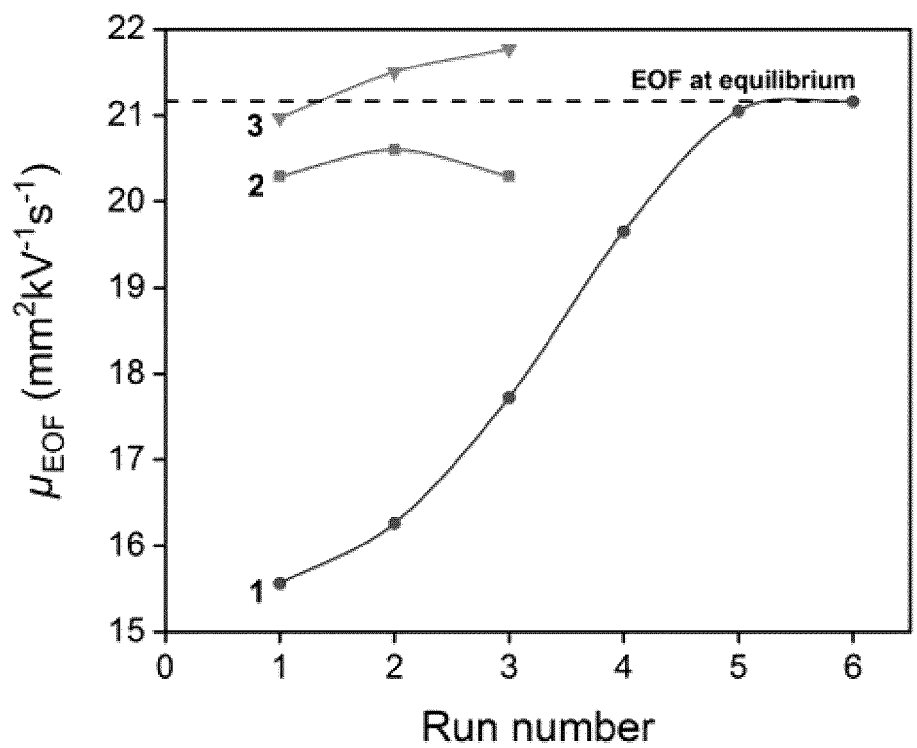
FIG. 13 shows the effect of different capillary pre-conditioning procedures (three different pre-conditioning protocols were evaluated) on the stability of EOF, represented by the value of $\mu_{EOF}$. Lines 1, 2, and 3 represent the results for standard pre-conditioning (Protocol 1), overnight pre-conditioning (Protocol 2), and shorter-than-overnight pre-conditioning (Protocol 3), respectively.

An overnight pre-conditioning procedure (Protocol 2) was then used to see if such a long time of treatment would facilitate reaching the buffer-surface equilibrium. The results showed that such treatment led to $\mu_{EOF}$ in the first CE run being very close to that of "equilibrium $\mu_{EOF}$" reached only after about 5-6 CE runs after using Protocol 1 (FIG. 33, Line 2). A faster pre-conditioning procedure (Protocol 3) provided $\mu_{EOF}$ of the first CE run equal to the saturation $\mu_{EOF}$ and stable EOF during the following CE runs (FIG. 13, Line 3). Protocol 3 provided stable EOF for a wide range of $\mu_{EOF}$ achieved by using running buffers with varying pH and $I_{RB}$.

Experiment 2

Materials, Procedures, and Equipment Used in Experiment 2

All chemicals utilized were manufactured by Sigma-Aldrich (Oakville, ON, Canada) unless otherwise stated. Fused-silica capillaries with inner and outer diameters of 75 and 360 μm, respectively, were manufactured by Molex Polymicro (Phoenix, AZ, USA). Bodipy (4,4-difluoro-4-bora-3a,4a-diaza-s-indacene) was produced by Life Technologies Inc. (Burlington, ON, Canada). Two sets of CE buffers were used. The first set of CE buffers was 50 mM Tris-HCl with NaCl ranging from 0 to 150 mM at pH 7.4. The second set of CE buffers was Tris-HCl with ionic strength of 191 mM at pH 7.4, 7.8 and 8.0. The sample buffer was the same as the CE buffer to prevent advert effects of buffer mismatch.

Accordingly, all dilutions of sample components used in CE experiments were done by adding the corresponding CE buffer.

Default Conditions for Measuring Mobilities of EOF:

All CE experiments were performed with a P/ACE MDQ™ apparatus (SCIEX, Concord, ON, Canada) equipped with a laser-induced fluorescence (LIF) detection system. Fluorescence was excited with a blue line (488 nm) of a solid-state laser and detected at 520 nm using a spectrally-optimized emission filter system. Uncoated fused-silica capillaries, with a total length of 50 cm and a 10.2 cm distance from one of the ends to the detection zone were used. Prior to each set of measurements for one CE buffer, the capillary was preconditioned with the method stated in Protocol 3. Between the runs with the same buffer, the capillary was only rinsed by the corresponding CE buffer for 3 min at 20.0 psi. The sample contained 500 nM Bodipy and was injected with a pressure pulse of 0.5 psi×10 s to yield a 10 mm long sample plug. The injected sample plug was propagated through the uncooled part of the capillary at the inlet by injecting a 5.7 cm long plug of the buffer with a pressure pulse of 0.3 psi×90 s. For $\mu_{EOF}$ measuring experiment, CE was carried out at an electric field of 200 V/cm (10 kV over 50 cm) for 20 min.

Results for Experiment 2

Figure 14A:
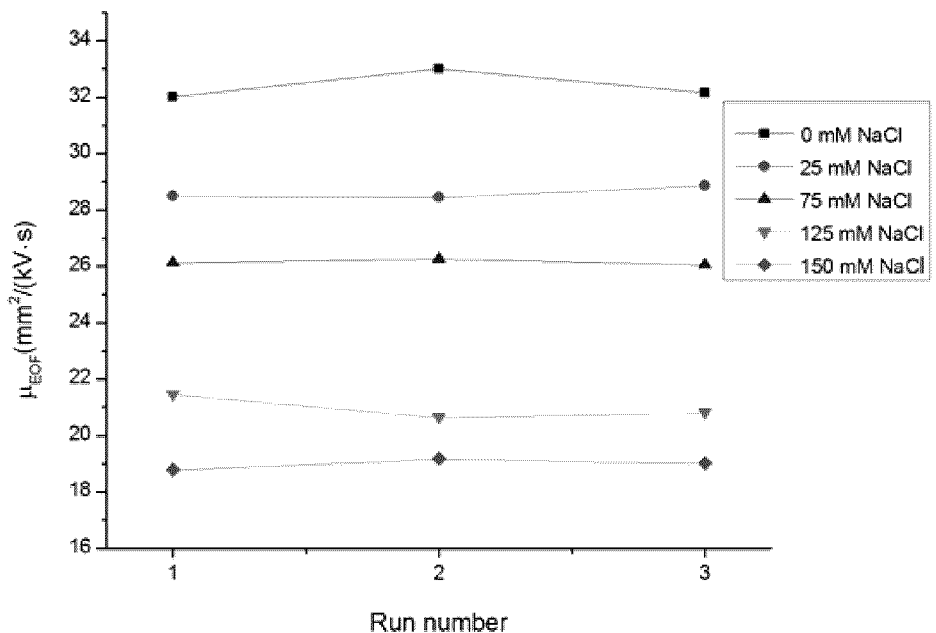
FIGS. 14A and 14B show the effect of pH and $I_{RB}$ of the running buffer on the stability of EOF in a capillary pre-conditioned according to Protocol 3. Panel A: EOF stability checking for 50 mM Tris-HCl with addition of about 0, 25, 75, 125, 150 mM NaCl at fixed pH value of about 7.4. According to the results, with the preconditioning method of protocol 3, the relative standard errors of $\mu_{EOF}$ for the followed three CE runs were all smaller than about 2.0%, which indicates the preconditioning method can be applicable to stabilize EOF for Tris-HCl buffer at about pH 7.4 with different ionic strength. Panel B: EOF stability checking for Tris-HCl with fixed ionic strength of about 191 mM at about pH 7.4, 7.8 and 8.0. Based on the experimental results, after the preconditioning method of protocol 3, the relative standard errors of $\mu_{EOF}$ for the followed six CE runs were all smaller than about 2.0% as well. This shows that the preconditioning method of protocol 3 can be applicable to stabilize EOF for Tris-HCl buffer at different pH.
Figure 14B:
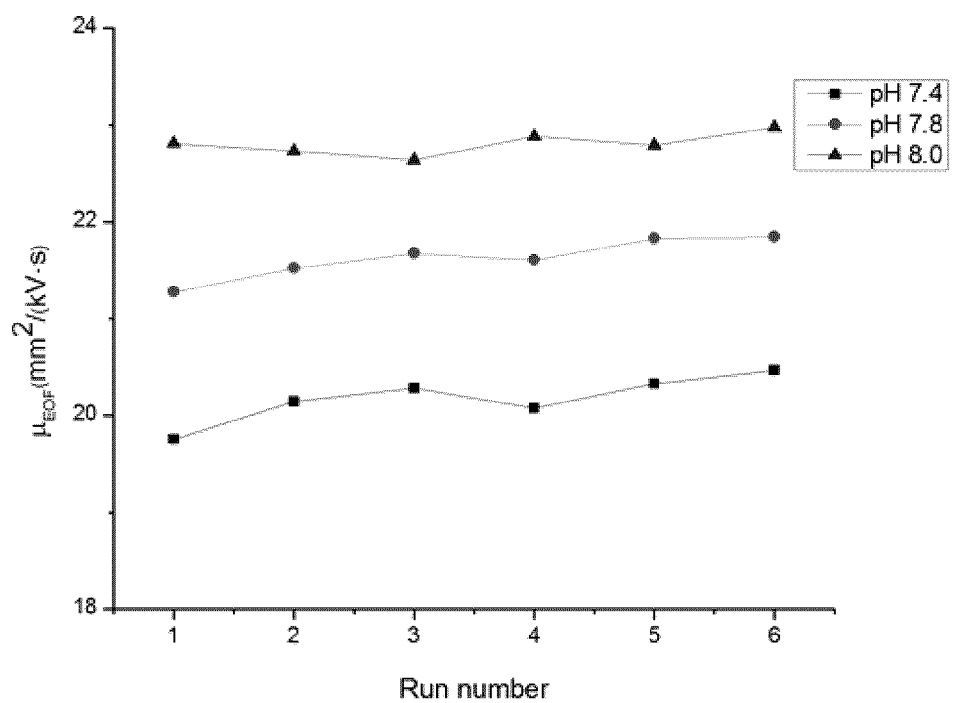

The stability of EOF in consecutive CE runs following capillary preconditioning by using Protocol 3 was studied to varying pH and $I_{RB}$ of the running buffer. The results of this study are shown in FIGS. 14A and 14B. Capillary pre-conditioning using Protocol 3 supported stable EOF for all running buffers studied. Example 2, thus, provided a capillary pre-conditioning protocol, Protocol 3, which supported the required stability of EOF in the binder-selection method.

Example 3: Influence of pH and Ionic Strength on Non-Binder Background

The effect of pH and ionic strength ($I_{RB}$) on the non-binder background was studied using a random-sequence DNA library as a general example of an oligonucleotide library.

Materials, Procedures, and Equipment used in Example 3

All chemicals utilized were manufactured by Sigma-Aldrich (Oakville, ON, Canada) unless otherwise stated. Fused-silica capillaries with inner and outer diameters of 75 and 360 μm, respectively, were manufactured by Molex Polymicro (Phoenix, AZ, USA). All DNA molecules were custom synthesized by Integrated DNA Technologies (Coralville, IA, USA). Bodipy (4,4-difluoro-4-bora-3a,4a-diazas-indacene) was produced by Life Technologies Inc. (Burlington, ON, Canada). For the DNA background study of varying $I_{RB}$, the CE buffer was 50 mM TrisHCl with NaCl ranging from 0 to 150 at pH 7.4, resulting in $I_{RB}$ ranging from 41 to 191 mM respectively. For the DNA background study of varying pH, the CE buffer was 50 mM TrisHCl with NaCl ranging from 150 to 186 mM and pH ranging from 7.4 to 9.0, resulting in constant $I_{RB}$=191 mM. The sample buffer was the same as the buffer to prevent advert effects of buffer mismatch. Accordingly, all dilutions of sample components used in CE experiments were done by adding the corresponding buffer.

DNA Sequences

A synthetic FAM-labeled DNA library (N40) with a 40-nt random region was used: 5'-FAM-CT ACG GTA AAT CGG CAG TCA-(N40)-AT CTG AAG CAT AGT CCA GGC-3'. The nucleotide sequence of the sense primer (uF) was 5'-CTACGGTAAATCGGCAGTCA-3' and the sequence of the anti-sense primer (uR) was 5'-GCCTGGAC-TATGCTTCAGAT-3'.

Default Conditions for CE and Fraction Collection

All CE experiments were performed with a P/ACE MDQ™ apparatus (SCIEX, Concord, ON, Canada) equipped with a laser-induced fluorescence (LIF) detection system. Fluorescence was excited with a blue line (488 nm) of a solid-state laser and detected at 520 nm using a spectrally-optimized emission filter system. Uncoated fused-silica capillaries, with a total length of 50 cm and a 10.2 cm distance from one of the ends to the detection zone were used. The two capillary ends were used as inlets interchangeably in experiments requiring different separation distances. Prior to every run, the capillary was rinsed successively with 0.1 M HCl, 0.1 M NaOH, deionized $H_2O$, and a run buffer for 3 min each. The sample contained 10 μM annealed oligonucleotides (melted at 90° C. for 2 min and gradually cooled down to 20° C. at a rate of 0.5° C./min) and 150 nM Bodipy. The sample mixture was injected with a pressure pulse of 0.5 psi×10 s to yield a 10-mm-long sample plug. The injected sample plug was propagated through the uncooled part of the capillary at the inlet by injecting a 5.7 cm long plug of the buffer with a pressure pulse of 0.3 psi×90 s. For fraction collection experiment, CE was carried out at an electric field of 200 V/cm (10 kV over 50 cm) for 64 min. Collection vials contained 20 μL of the buffer each and were switched every 2 min; 32 fractions were collected.

Quantitative PCR

DNA in the collected fractions was amplified and quantitated by qPCR using a CFX Connect™ instrument from Bio-rad. q-PCR reagent mixture was prepared by combining IQ SYBR Green Supermix from Bio-Rad (Mississauga, ON, Canada) with unlabeled DNA primers at final concentrations of 1×SYBR Green Supermix, 100 nM uF, and 100 nM uR. qPCR reaction mixture was prepared by adding 18 μL of the qPCR reagent mixture to a 2-μL aliquot of each fraction immediately before thermocycling. The thermocycling protocol was: 95° C. for 3 min, 95° C. for 10 s (denaturation), 56° C. for 10 s (annealing), 72° C. for 10 s (extension), followed by a plate read at 72° C. and a return to the denaturation step (bypassing the 95° C.×3 min step) for a total of 43 cycles. All reactions were performed in duplicates.

Experiment 1

Figure 15A:
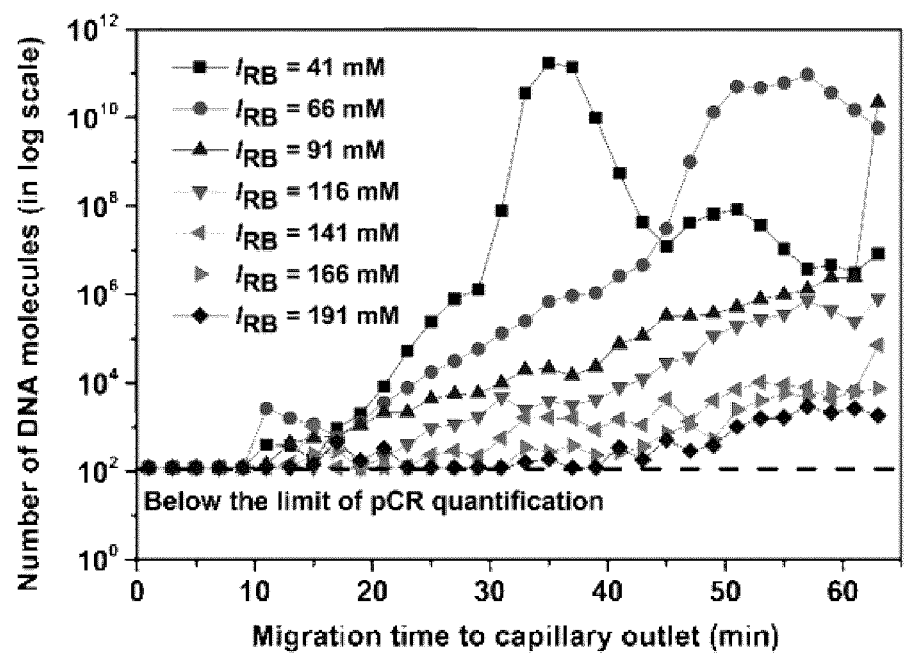
FIGS. 15A and 15B show the effect on the DNA background of $I_{RB}$ in a Tris-HCl running buffer about pH 7.0 (FIG. 15A) and of pH in a Tris-HCl running buffer with about $I_{RB}$=191 mM (FIG. 15B). The sample contained about 10 µM DNA and about 150 nM Bodipy. Separation distance was about 34 cm. Fractions were collected every 2 min and concentrations of DNA in them were determined with qPCR and used to calculate DNA quantities in these fractions. These quantities are shown on the y-axis in the graphs.

The effect on the DNA background of varying $I_{RB}$ (in a range of 41 to 191 mM) at a constant pH 7.4 of the running buffer was studied. The sample was 10 μM library of random-sequence DNA and 150 nM Bodipy (uncharged fluorophore, EOF marker) in the running buffer. The sample was injected and propagated by CE followed by collecting fractions and quantifying DNA in them, as described in the methods section above. The results are shown in FIG. 15A. The observed trend is similar to that found for pH 7.0 (see FIG. 7). The DNA background was found to be higher at pH 7.4 than at pH 7.

Experiment 2

Figure 15B:
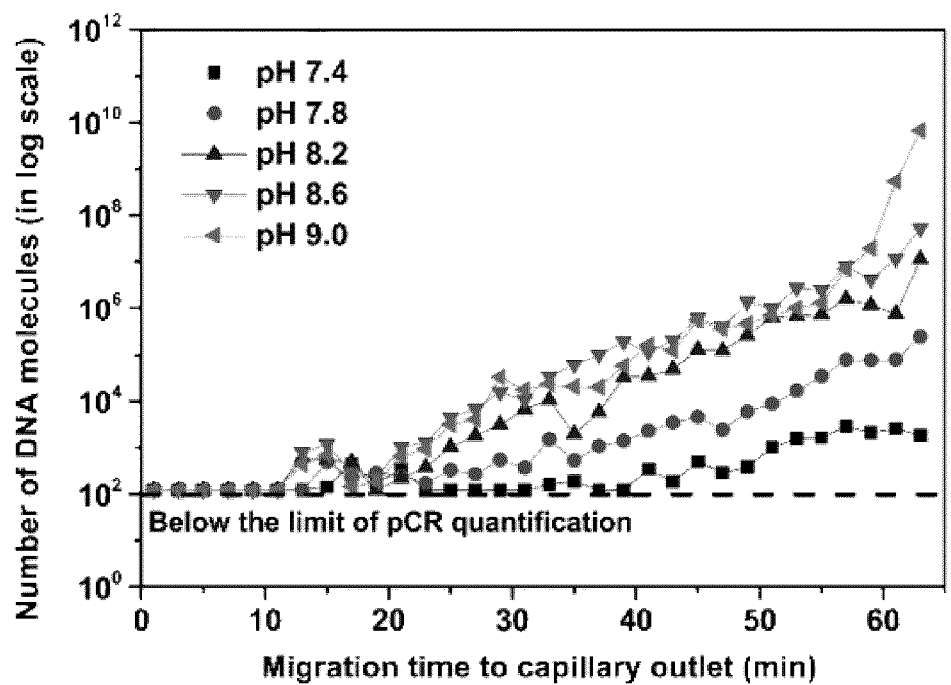

The effect on the DNA background of varying pH of the running buffer (in a range of 7.4 to 9.0) at a constant $I_{RB}$=191 mM was studied. As in experiment 1, the sample was 10 μM library of random-sequence DNA and 150 nM Bodipy (uncharged fluorophore, EOF marker) in the running buffer. The sample was injected and propagated by CE followed by collecting fractions and quantifying DNA in them, as described in the methods section above. The results are shown in FIG. 15B. The DNA background appeared to increase with increasing pH, therefore, changing buffer pH was as an effective way to control DNA background as changing $I_{RB}$. DNA background can be controlled (via changing pH and $I_{RB}$) which provides additional flexibility for choosing a running buffer suitable for the target, e.g. if the target is a protein, sensitive to pH and/or $I_{RB}$.

Example 4: Selection of DNA Aptamers for Streptavidin as a Target

Figure 16:
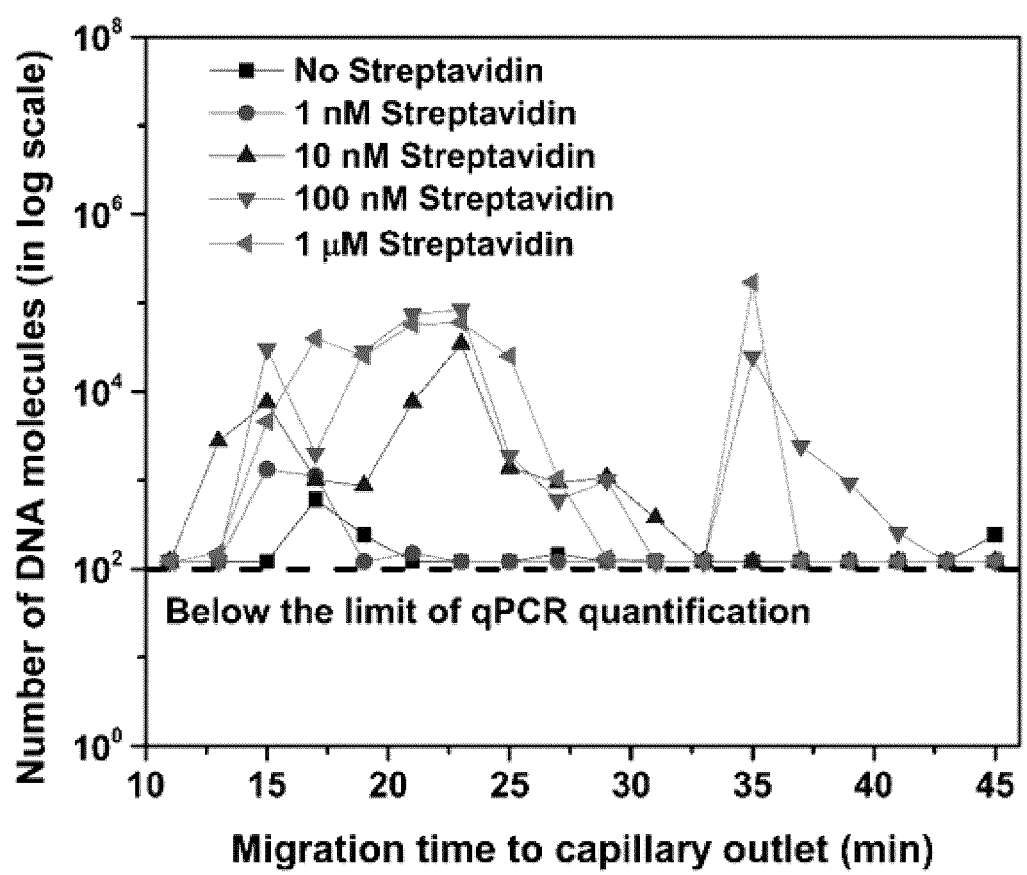
FIG. 16 shows IFCE-based partitioning of DNA binders of Streptavidin protein from an unbound library. The sampled equilibrium mixture had a volume of about 47 nL and contained about 10 µM random-sequence DNA library with varying concentrations of Streptavidin ranging from about 1 nM to about 1 µM. Separation distance was about 34 cm.

The conditions that were optimized in the above examples were used to select DNA aptamers for Streptavidin. One round selection of aptamers was repeated by three, independent, persons for varying concentrations of the target in the equilibrium mixture. Detectable peaks of target-binder complexes were revealed in all selections (FIG. 16), confirming the high efficiency of binder selection with the CE-based method.

Materials, Procedures, and Equipment Used in Example 4

All chemicals utilized were manufactured by Sigma-Aldrich (Oakville, ON, Canada) unless otherwise stated. Fused-silica capillaries with inner and outer diameters of 75 and 360 μm, respectively, were manufactured by Molex Polymicro (Phoenix, AZ, USA). Streptavidin protein was purchased from New England Biolabs (Ipswich, MA, USA). All DNA molecules were custom synthesized by Integrated DNA Technologies (Coralville, IA, USA). Bodipy (4,4-difluoro-4-bora-3a,4a-diaza-s-indacene) was produced by Life Technologies Inc. (Burlington, ON, Canada). The CE buffer was 50 mM Tris-HCl, 100 mM NaCl pH 7.0. The sample buffer was the same as the buffer to prevent advert effects of buffer mismatch. Accordingly, all dilutions of sample components used in CE experiments were done by adding the corresponding buffer.

DNA Sequences

A synthetic FAM-labeled DNA library (N40) with a 40-nt random region was used: 5'-FAM-CT ACG GTA AAT CGG CAG TCA-(N40)-AT CTG AAG CAT AGT CCA GGC-3'. The nucleotide sequence of the sense primer (uF) was 5'-CTACGGTAAATCGGCAGTCA-3' and the sequence of the anti-sense primer (uR) was 5'-GCCTGGAC-TATGCTTCAGAT-3'.

Default Conditions for CE and Fraction Collection

All CE experiments were performed with a P/ACE MDQ™ apparatus (SCIEX, Concord, ON, Canada) equipped with a laser-induced fluorescence (LIF) detection system. Fluorescence was excited with a blue line (488 nm) of a solid-state laser and detected at 520 nm using a spectrally-optimized emission filter system. Uncoated fused-silica capillaries, with a total length of 50 cm and a 10.2 cm distance from one of the ends to the detection zone were used. The two capillary ends were used as inlets interchangeably in experiments requiring different separation distances. Prior to every run, the capillary was rinsed successively with 0.1 M HCl, 0.1 M NaOH, deionized H$_2$O, and a run buffer for 3 min each. The sample contained 10 µM annealed oligonucleotides (melted at 90° C. for 2 min and gradually cooled down to 20° C. at a rate of 0.5° C./min) and 150 nM Bodipy. When specified, the sample also contained Strepavidin protein with concentration ranging from 1 nM to 1 µM. The sample mixture was incubated for 30 min at a room temperature (22-24° C.) and then injected with a pressure pulse of 0.5 psi×10 s to yield a 10 mm long sample plug. The injected sample plug was propagated through the uncooled part of the capillary at the inlet by injecting a 5.7 cm long plug of the buffer with a pressure pulse of 0.3 psi×90 s. For fraction collection experiment, CE was carried out at an electric field of 200 V/cm (10 kV over 50 cm) for 64 min. Collection vials contained 20 µL of the buffer each and were switched every 2 min; 32 fractions were collected.

Quantitative PCR

DNA in the collected fractions was amplified and quantitated by qPCR using a CFX Connect™ instrument from Bio-rad. q-PCR reagent mixture was prepared by combining IQ SYBR Green Supermix from Bio-Rad (Mississauga, ON, Canada) with unlabeled DNA primers at final concentrations of 1×SYBR Green Supermix, 100 nM uF, and 100 nM uR. qPCR reaction mixture was prepared by adding 18 µL of the qPCR reagent mixture to a 2-µL aliquot of each fraction immediately before thermocycling. The thermocycling protocol was: 95° C. for 3 min, 95° C. for 10 s (denaturation), 56° C. for 10 s (annealing), 72° C. for 10 s (extension), followed by a plate read at 72° C. and a return to the denaturation step (bypassing the 95° C.×3 min step) for a total of 43 cycles. All reactions were performed in duplicates.

What is claimed is:

1. A capillary electrophoresis method comprising:
    selecting an electroosmotic flow (EOF) in a capillary such that at least one target-binder (TB) complex has a target-binder velocity vector ($v_{TB}$) co-directed with an electric field vector (E) and at least one non-binder (N) has a non-binder velocity vector ($v_N$) in the opposite direction to the electric field vector (E);
    introducing a sample comprising the at least one target-binder (TB) complex, the at least one non-binder (N), and at least one running buffer into a capillary inlet of the capillary;
    applying an electric field directed from the capillary inlet to a capillary outlet of the capillary to separate the at least one target-binder (TB) complex from the at least one non-binder (N); and
    detecting the at least one target-binder complex,
    wherein the electroosmotic flow is adjusted so that the equation:

$$(k_N/k_B) \geq 100(N/B)_0$$

is satisfied, where $k_N$ is the transmittance for the at least one non-binder, $k_B$ is the transmittance for the at least one binder, and $(N/B)_0$ is the at least one non-binder to at least one binder molar ratio prior to applying the electric field.

2. The capillary electrophoresis method of claim 1, wherein the selected EOF is achieved by adjusting pH and/or ionic strength of the at least one running buffer; and/or wherein the pH is selected such that there is minimal degradation of the at least one target-binder (TB) complex, optionally, wherein the pH is about 5 to about 9, about 6 to about 8, or about 6.5 to about 7.5.

3. The capillary electrophoresis method of claim 2, wherein the at least one running buffer has a pH and/or ionic strength that is similar to physiological pH and/or ionic strength; and/or
    wherein the EOF is adjusted by increasing or decreasing an ionic strength of the at least one running buffer; and/or
    wherein the at least one running buffer further comprises at least one salt to modulate the ionic strength of the at least one running buffer, optionally,
        the at least one salt is selected from alkali metal salts, alkaline earth metal salts, or combination thereof; and/or
        the at least one salt is selected from the group consisting of sodium chloride, sodium iodide, sodium bromide, lithium bromide, lithium iodide, potassium phosphate, sodium bicarbonate, calcium chloride, calcium iodide, calcium bromide, calcium phosphate, calcium bicarbonate, magnesium chloride, magnesium iodide, magnesium bromide, magnesium phosphate, magnesium bicarbonate and a combination thereof; and/or
        the at least one salt comprises sodium chloride; optionally,
    wherein the concentration of sodium chloride is less than about 1000 mM or the concentration of sodium chloride is about 10 mM to about 200 mM.

4. The capillary electrophoresis method of claim 3, wherein the ionic strength of the at least one running buffer is about 128 mM to about 192 mM.

5. The capillary electrophoresis method of claim 1, wherein increasing ionic strength of the at least one running buffer leads to an increased buffer temperature in the capillary, and decreasing voltage leads to a decreased buffer temperature in the capillary;
    wherein, when at least one target of the at least one target-binder complex has a lower molecular weight compared to another target of a target-binder complex, the ionic strength is adjusted lower or the pH is adjusted higher to achieve the selected EOF; and/or
    wherein, the at least one binder and the at least one non-binder is an oligonucleotide and when the length of the oligonucleotide is longer compared to another binder and non-binder, the ionic strength is adjusted lower or the pH is adjusted higher to achieve the selected EOF.

6. The capillary electrophoresis method of claim 1, wherein separating the at least one target-binder (TB) complex from the at least one non-binder (N) occurs in a single cycle.

7. The capillary electrophoresis method of claim 1, wherein $k_N$ is less than $1 \times 10^{-6}$; or
    wherein $k_N$ is from about $6 \times 10^{-10}$ to about $8 \times 10^{-6}$; or
    wherein $k_N$ is less than about $6 \times 10^{-10}$.

8. The capillary electrophoresis method of claim 7, wherein $k_B$ is about 1.

9. The capillary electrophoresis method of claim 1, wherein $|\mu_N| > |\mu_{EOF}| > |\mu_{TB}|$ is satisfied where $\mu_N$ is a non-binder mobility vector, $\mu_{EOF}$ is a mobility vector of the electroosmotic flow, and $\mu_{TB}$ is the at least one target-binder complex mobility vector; optionally, $|\mu_N| > |\mu_{EOF}| > |\mu_{TB}|$ is satisfied by increasing an ionic strength of the at least one running buffer.

10. The capillary electrophoresis method of claim 1, wherein the selected EOF is achieved by adjusting pH and/or ionic strength of the at least one running buffer such that $v_{TB}=-v_N$ and $v_{TB}$ is co-directed with E, and EOF mobility vector, $M_{EOF}$, that provides $v_{TB}=-v_N$ is:

$$M_{EOF}=-\tfrac{1}{2}(\mu_N+\mu_{TB}) \quad \text{eq. 4}$$

$\mu_N$ is $\mu_{DNA}\approx$ about 19 to about 27 mm²/(KV s)
$\mu_{TB}$ is calculated from:

$$\mu_{TB} = F(\mu_N, d_T, L_{DNA}) = \frac{d_T^2 \mu_T + (d_{dsDNA}L_{dsDNA} + d_{ssDNA}L_{ssDNA})\mu_N}{d_T^2 + d_{dsDNA}L_{dsDNA} + d_{ssDNA}L_{ssDNA}} \quad \text{eq. 5}$$

$d_T$ is the diameter of the target;
$v_{TB}$ is target-binder (TB) complex velocity vector;
$v_N$ is non-binder (N) velocity vector;
the at least one binder and the at least one non-binder comprise at least one DNA moiety, wherein the at least one DNA moiety is DNA, ssDNA, and/or dsDNA;
$\mu_T$ is the electrophoretic mobility of the target, which is determined by running the target itself in CE along with an EOF marker (neutral molecule):
$\mu_T=(v_T-v_{EOF})/E$, and $v_T$ and $v_{EOF}$ are determined by dividing the capillary length, which is from a point where the sample was located at the start time of electrophoresis to a detection point, $I_{cap}$, by the migration time of a peak of the target, $t_T$, and the EOF marker, $t_{EOF}$: $v_T=I_{cap}/t_T$ and $v_{EOF}=I_{cap}/t_{EOF}$, respectively;
$d_{dsDNA}$ is about 2.6 nm and $d_{ssDNA}$ is about 1.6 nm;
for the DNA moiety, the lengths of moieties are calculated by $L_{dsDNA}=b_{dsDNA}\times n_{dsDNA}$, $L_{ssDNA}=b_{ssDNA}\times n_{ssDNA}$, where $b_{dsDNA}=0.34$ nm and $b_{ssDNA}=0.43$ nm are the lengths of dsDNA and ssDNA monomers and $n_{dsDNA}$ and $n_{ssDNA}$ are numbers of nucleotides in all double-stranded regions and all single-stranded regions, respectively;
$M_{EOF}$ being calculated and adjusted to provide $v_{TB}=-v_N$; the pH and/or $I_{RB}$ of the running buffer is then determined by measuring $\mu_{EOF}$, which is a mobility vector of the electroosmotic flow, for a fixed pair of pH and $I_{RB}$ as a starting point and, if $\mu_{EOF}>M_{EOF}$ then $\mu_{EOF}$ is decreased by decreasing pH and/or increasing $I_{RB}$; if $\mu_{EOF}<M_{EOF}$ then $\mu_{EOF}$ is increased by increasing pH and/or decreasing/RB.

11. The capillary electrophoresis method of claim 1, wherein separation of the at least one non-binder from the at least one target-binder complex is improved in comparison to other methods of separation used in systematic evolution of ligands by exponential enrichment (SELEX).

12. The capillary electrophoresis method of claim 1, wherein selecting the electroosmotic flow reduces non-binder background; and/or
wherein adjusting the electroosmotic flow reduces non-binder background detected at the capillary outlet.

13. The capillary electrophoresis method of claim 1, further comprising introducing at least one running buffer into the capillary inlet after introducing the sample;
wherein the sample and the at least one running buffer are introduced into the capillary via capillary action, pressure, siphoning, or electrokinetically between the capillary inlet and the capillary outlet; and/or
wherein the sample and the at least one running buffer are introduced into the capillary by creating a pressure difference between the capillary inlet and the capillary outlet.

14. The capillary electrophoresis method of claim 1, wherein the sample is propagated from the capillary inlet by the pressure difference before an electric field is applied; optionally, the propagation reduces the separation time without having to change the capillary length or the electric field.

15. The capillary electrophoresis method of claim 1, wherein the at least one binder and the at least one non-binder are selected from oligonucleotide tagged molecules and/or oligonucleotides; and/or
wherein an oligonucleotide library comprises the at least one binder and the at least one non-binder; optionally, the oligonucleotide library comprises a random-sequence oligonucleotide library; the oligonucleotide library comprises natural (unmodified) oligonucleotides; the oligonucleotide library comprises modified oligonucleotides; and/or the oligonucleotide library comprises a library of oligonucleotide-encoded molecules; optionally, the oligonucleotide-encoded molecules comprise DNA-encoded drug-like molecules.

16. The capillary electrophoresis method of claim 15, wherein the oligonucleotide library comprises aptamers; and/or
wherein the oligonucleotide library comprises RNA or single-stranded DNA oligonucleotides.

17. The capillary electrophoresis method of claim 15, wherein the tagging oligonucleotide of the oligonucleotide tagged molecule and/or oligonucleotide is amplified; optionally, PCR is used to amplify.

18. The capillary electrophoresis method of claim 1, wherein the at least one binder is capable of forming a target-binder complex that has an electrophoretic shift compared to the at least one non-binders.

19. The capillary electrophoresis method of claim 1, wherein at least one target of the at least one target-binder complex is selected from the group comprising proteins, peptides, nucleic acids, amino acids, nucleosides, antibodies, antibody fragments, antibody ligands, peptide nucleic acids, small organic molecules, lipids, hormones, drugs, enzymes, lectin, cell adhesion molecule, antibody epitope, enzyme substrates, enzyme inhibitors, coenzymes, inorganic molecules, carbohydrates, such as polysaccharides and monosaccharides, or a combination thereof.

20. The capillary electrophoresis method of claim 1, wherein the at least one binder further comprises a detectable moiety, wherein the detectable moiety is selected from the group consisting of a dye, a quantum dot, a radiolabel, an electrochemical functional group, an enzyme, an enzyme substrate, a ligand and a receptor.

21. The capillary electrophoresis method of claim 1, wherein the target comprises two or more targets bonded together to provide a greater molecular weight to increase separation of the target-binder complex(es) from the at least one non-binder and the selection of at least one binder for more than one target, simultaneously.

22. The capillary electrophoresis method of claim 1, wherein the sample comprises the at least one non-binder and at least one target the at least one target-binder complex, which are permitted to equilibrate to provide the at least one non-binder and the at least one target-binder complex.

23. The capillary electrophoresis method of claim 1, wherein the sample is introduced into the capillary as a plug shorter than 10% of the capillary length.

24. The capillary electrophoresis method of claim 1, wherein detecting the at least one target-binder complex comprises collecting fractions and analyzing the fractions to identify the at least one binder; optionally, the analyzing comprises using quantitative polymerase chain reaction (qPCR) and/or the results of the qPCR analysis are used to determine the at least one binder distribution among the collected fractions.

25. The capillary electrophoresis method of claim 1, wherein the electric field is applied by a high voltage power source connected to an anode placed at the capillary inlet and a cathode placed at the capillary outlet; optionally, the applied electric field is from about 50 to about 600 V/cm.

26. The capillary electrophoresis method of claim 1, wherein the detecting of the at least one target-binder complex comprises using a detector; optionally, the detector is an optical spectrometer or qPCR.

27. The capillary electrophoresis method of claim 26, wherein the optical spectrometer comprises a light-absorbance spectrometer or a fluorescence spectrometer.

28. The capillary electrophoresis method of claim 1, further comprising preparing the sample comprising combining at least one binder, at least one non-binder and at least one target of the at least one target-binder complex under conditions to form the at least one target-binder complex and the at least one non-binder; optionally, further comprises incubating.

29. The capillary electrophoresis method of claim 1, wherein the at least one target-binder complex is separated from the at least one non-binder.

30. The capillary electrophoresis method of claim 1, wherein the electroosmotic flow is adjusted so that the target-binder complexes have a velocity of $v_{TB}$ and the non-binders have a velocity of $v_N$ follow: $v_{TB}>0>v_N$.

31. The capillary electrophoresis method of claim 1, wherein the capillary is pre-conditioned to provide a stable EOF; optionally, the stable EOF has a constant $\mu_{EOF}$ in consecutive CE runs.

32. The capillary electrophoresis method of claim 1, wherein the capillary is pre-conditioned by a treatment comprising consecutive rinsing.

33. The capillary electrophoresis method of claim 32, wherein the consecutive rinsing comprises rinsing with i) at least one alcohol, ii) at least one acid, iii) at least one base, iv) at least one water, and then v) at least one running buffer, and repeating steps ii) to iv) at least once.

34. The capillary electrophoresis method of claim 33, further comprising applying voltage with the running buffer.

* * * * *